United States Patent
Park et al.

(10) Patent No.: US 10,183,050 B2
(45) Date of Patent: Jan. 22, 2019

(54) BEAN LEAVES OR BEAN STEMS HAVING HIGH ISOFLAVONE DERIVATIVES CONTENT AND METHOD FOR PREPARING SAME

(71) Applicant: INDUSTRY-ACADEMIC COOPERATION FOUNDATION GYEONGSANG NATIONAL UNIVERSITY, Gyeongsangnam-do (KR)

(72) Inventors: Ki Hun Park, Gyeongsangnam-do (KR); Heung Joo Yuk, Gyeongsangnam-do (KR); Yeong Hun Song, Gyeongsangnam-do (KR)

(73) Assignee: INDUSTRY-ACADEMIC COOPERATION FOUNDATION GYEONGSANG NATIONAL UNIVERSITY, Gyeongsangnam-do (KR)

( * ) Notice: Subject to any disclaimer, the term of this patent is extended or adjusted under 35 U.S.C. 154(b) by 400 days.

(21) Appl. No.: 15/179,720

(22) Filed: Jun. 10, 2016

(65) Prior Publication Data

US 2016/0317597 A1  Nov. 3, 2016

Related U.S. Application Data

(63) Continuation of application No. PCT/KR2014/011493, filed on Nov. 27, 2014.

(30) Foreign Application Priority Data

Dec. 13, 2013 (KR) .................. 10-2013-0155430
Jul. 2, 2014   (KR) .................. 10-2014-0082481

(51) Int. Cl.

| | |
|---|---|
| *A61K 36/48* | (2006.01) |
| *A01N 57/20* | (2006.01) |
| *A01N 63/00* | (2006.01) |
| *A61K 8/97* | (2017.01) |
| *A61K 31/352* | (2006.01) |
| *A61K 31/704* | (2006.01) |
| *A61K 36/484* | (2006.01) |
| *A61Q 19/08* | (2006.01) |
| *A23L 33/105* | (2016.01) |
| *A01H 5/10* | (2018.01) |
| *A61Q 19/00* | (2006.01) |

(52) U.S. Cl.
CPC .............. *A61K 36/48* (2013.01); *A01H 5/10* (2013.01); *A01N 57/20* (2013.01); *A01N 63/00* (2013.01); *A23L 33/105* (2016.08); *A61K 8/97* (2013.01); *A61K 31/352* (2013.01); *A61K 31/704* (2013.01); *A61K 36/484* (2013.01); *A61Q 19/00* (2013.01); *A61Q 19/007* (2013.01); *A61Q 19/08* (2013.01); *A23V 2002/00* (2013.01); *A61K 2236/333* (2013.01); *A61K 2800/70* (2013.01)

(58) Field of Classification Search
None
See application file for complete search history.

(56) References Cited

U.S. PATENT DOCUMENTS

2007/0207224 A1   9/2007   Ng et al.

FOREIGN PATENT DOCUMENTS

| | | |
|---|---|---|
| DE | 10 2004 020 712 A1 | 11/2005 |
| EP | 1 038 531 A2 | 9/2000 |
| JP | 2000-262244 A1 | 9/2000 |
| JP | 2005-523721 A1 | 8/2005 |
| KR | 1020050104097 A | 11/2005 |
| KR | 1020070028776 A | 3/2007 |
| KR | 1020110009402 A | 1/2011 |
| KR | 1020120136164 A | 12/2012 |
| WO | WO 2005-074710 | 8/2005 |
| WO | WO 2005/074710 A1 | 8/2005 |

OTHER PUBLICATIONS

Goyal and Ramawat "Ethrel treatment enhanced isoflavonoids accumulation in cell suspension cultures of *Pueraria tuberosa*, a woody legume," *Acta Physiol Plant* 30:849-853 (2008).

*Primary Examiner* — Michael Barker
(74) *Attorney, Agent, or Firm* — Klarquist Sparkman, LLP

(57) ABSTRACT

The present invention relates to soybean leaves or soybean stems having high isoflavone derivative content, and a method for preparing the same. Specifically, by finding that soybean leaves or soybean stems treated with ethylene and ethephon, i.e. a ethylene donor, show significantly increased isoflavone derivative content, the method for preparing the soybean leaves or soybean stems having high isoflavone derivative content and the soybean leaves or soybean stems having high isoflavone derivative content prepared by using the method can be useful as functional foods and medicinal materials for diseases due to estrogen imbalance and lack of the antioxidative activity.

14 Claims, 16 Drawing Sheets

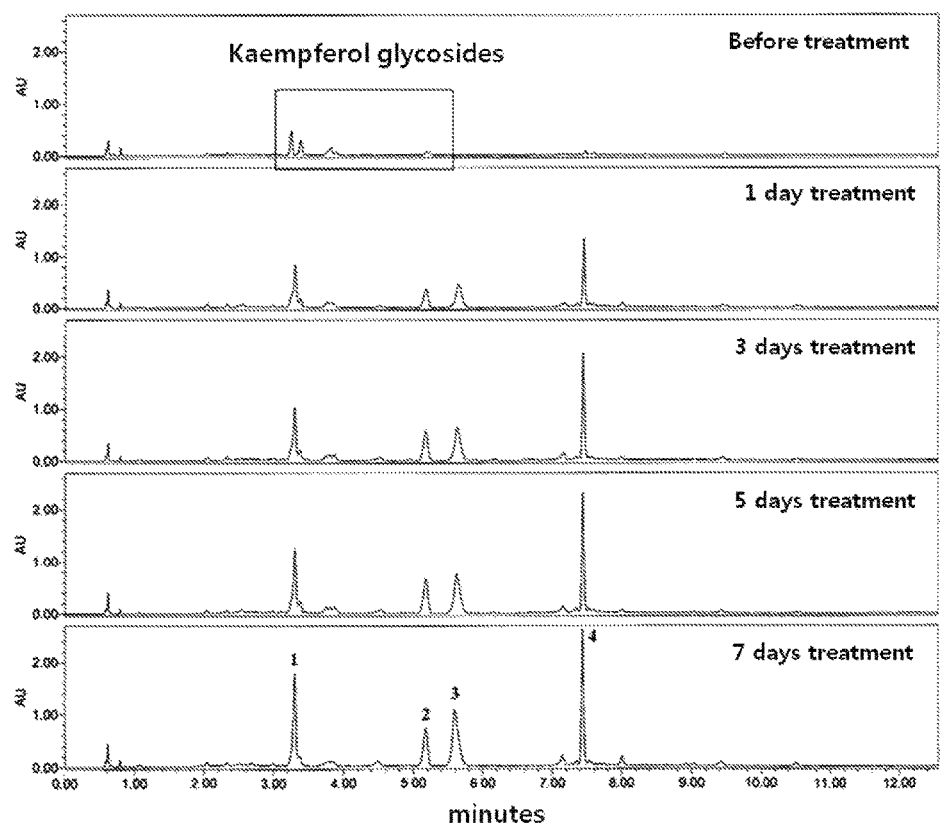
[Figure 1]

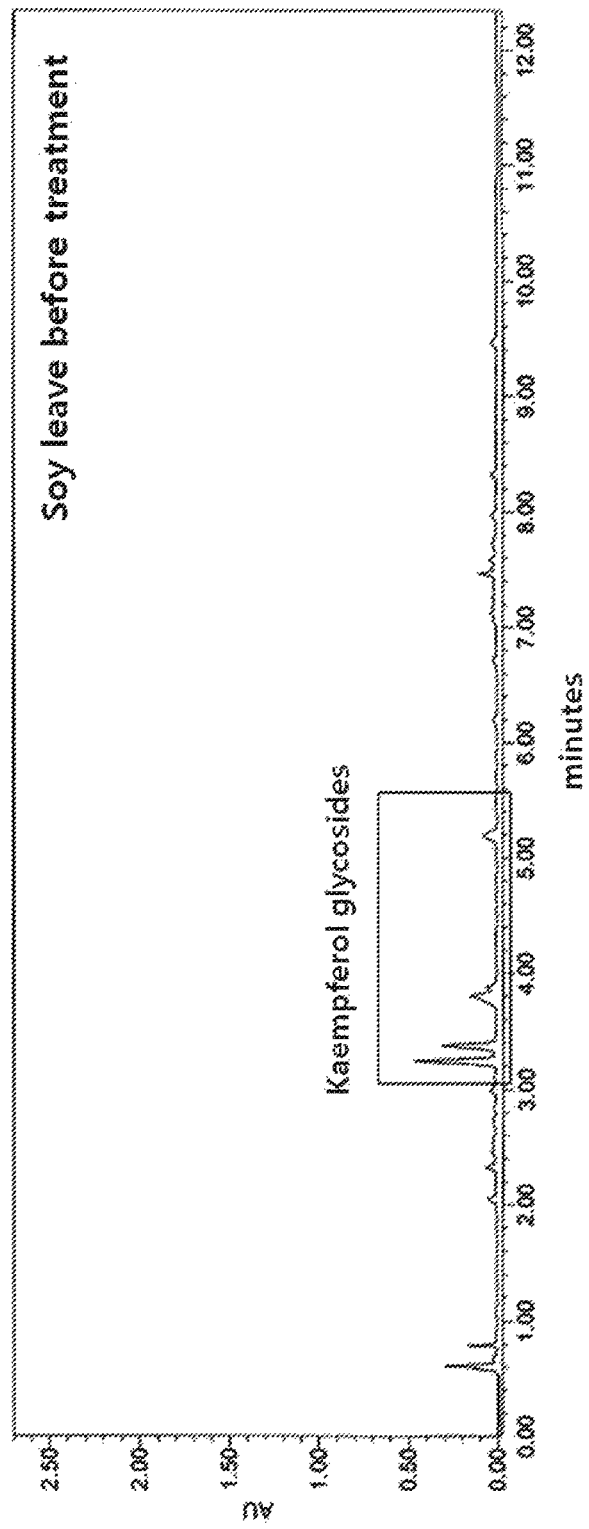
[Figure 2]

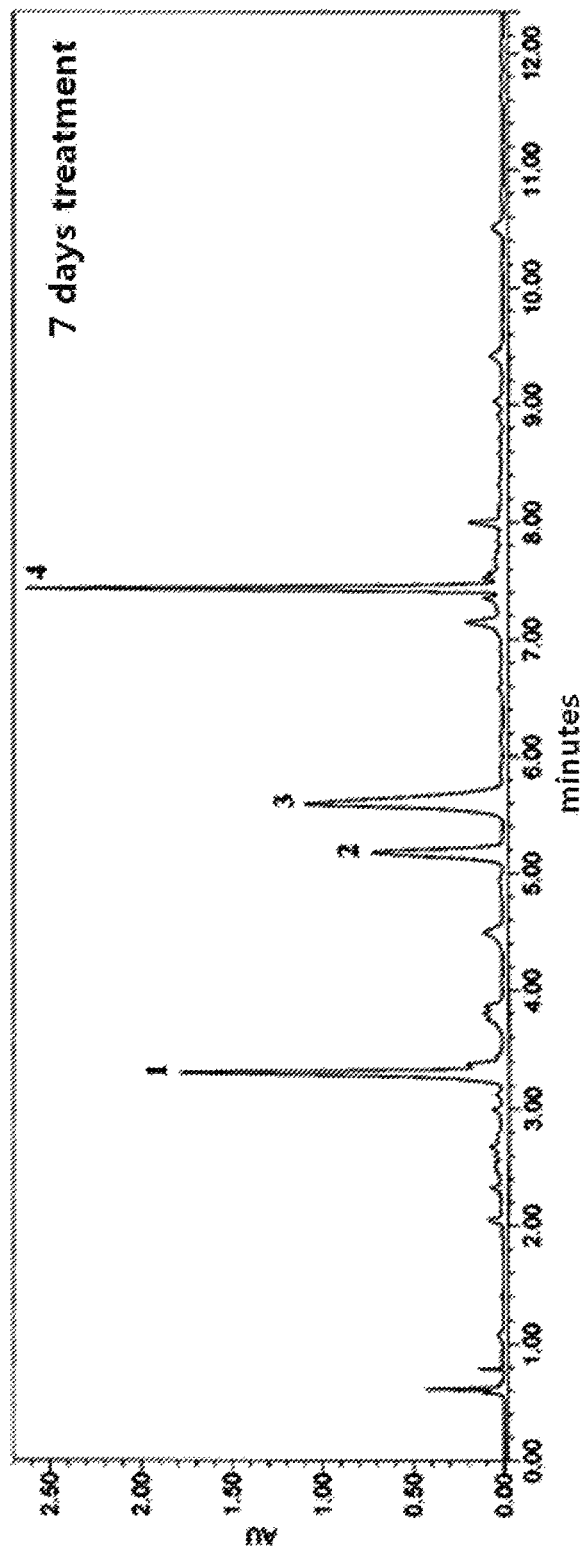
[Figure 3]

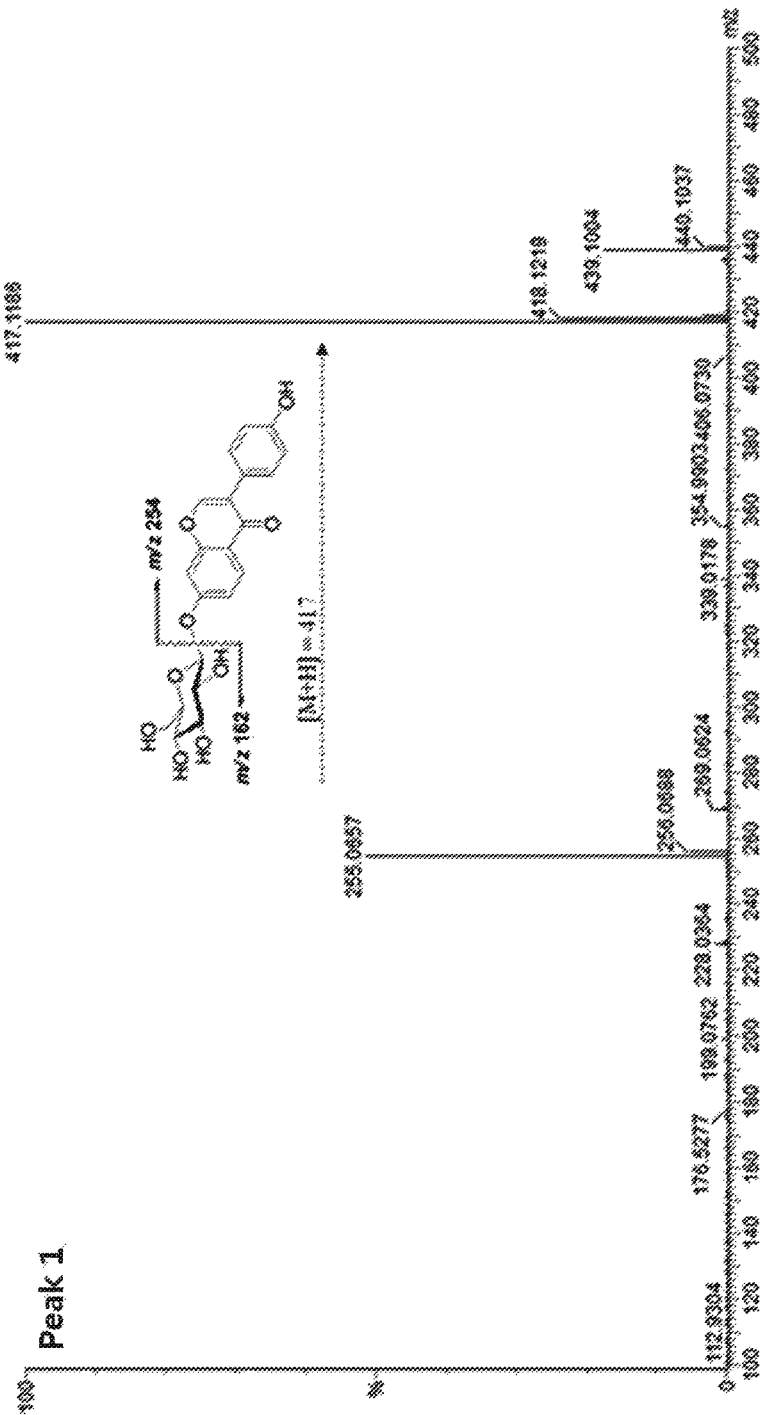
[Figure 4]

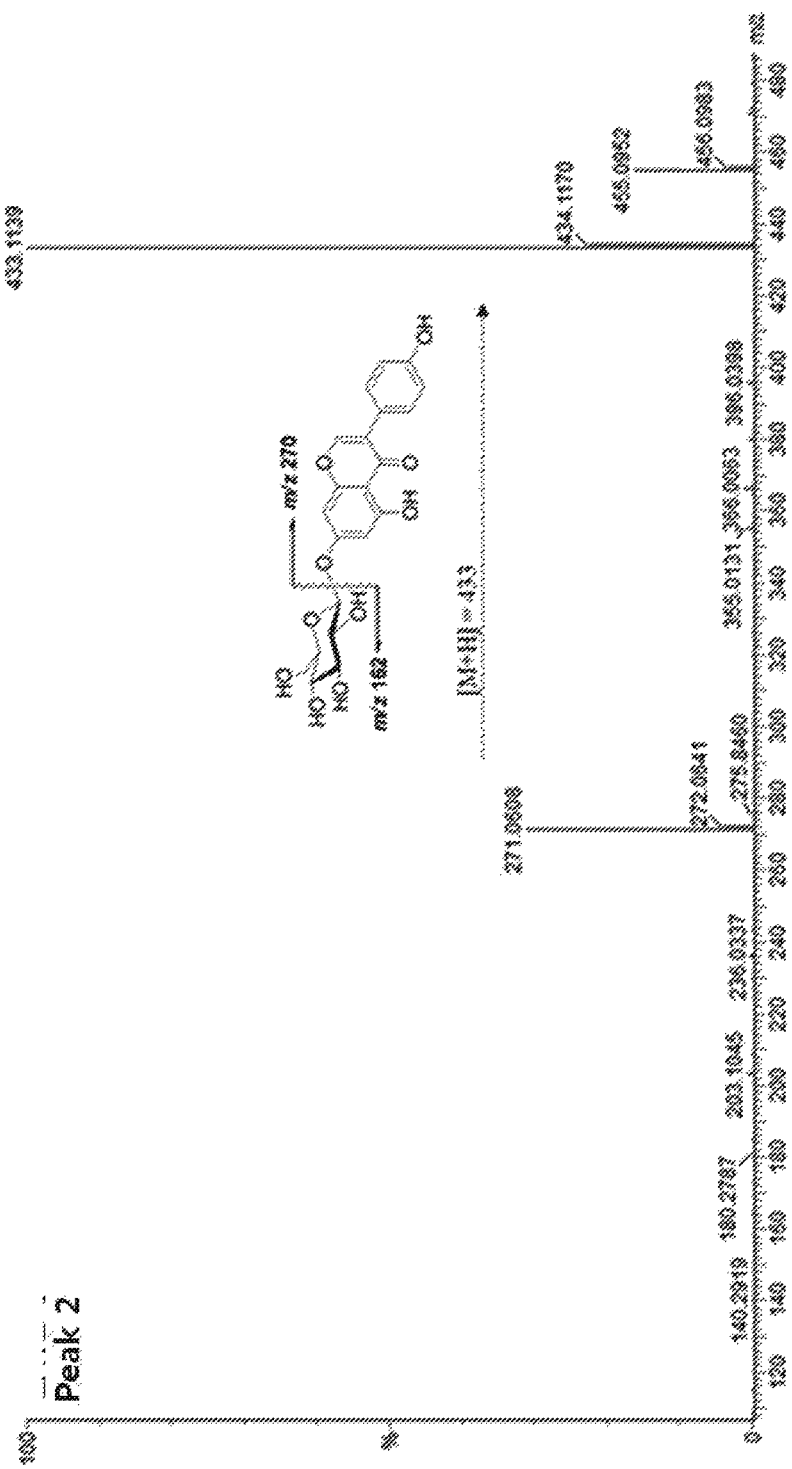
[Figure 5]

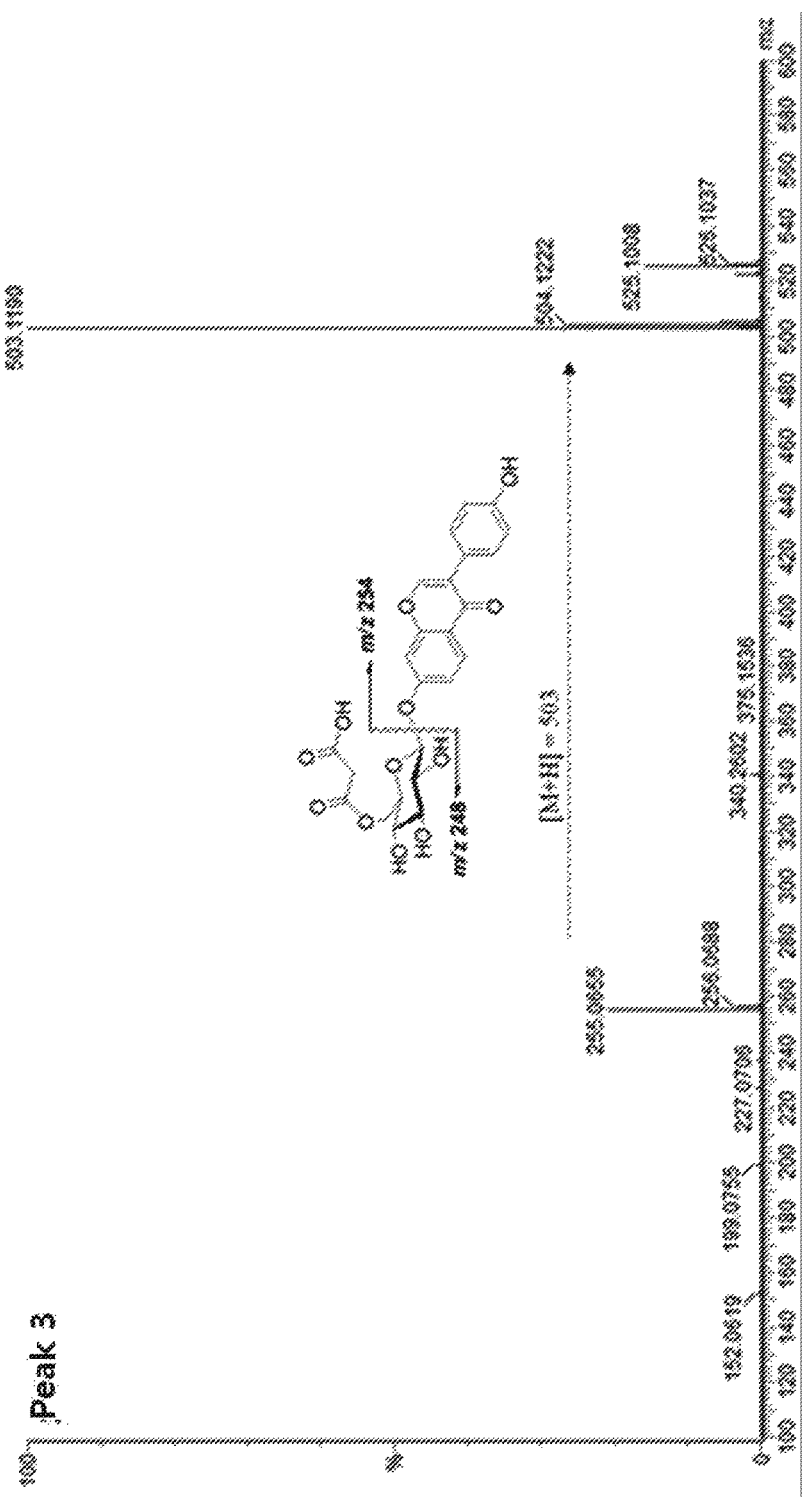
[Figure 6]

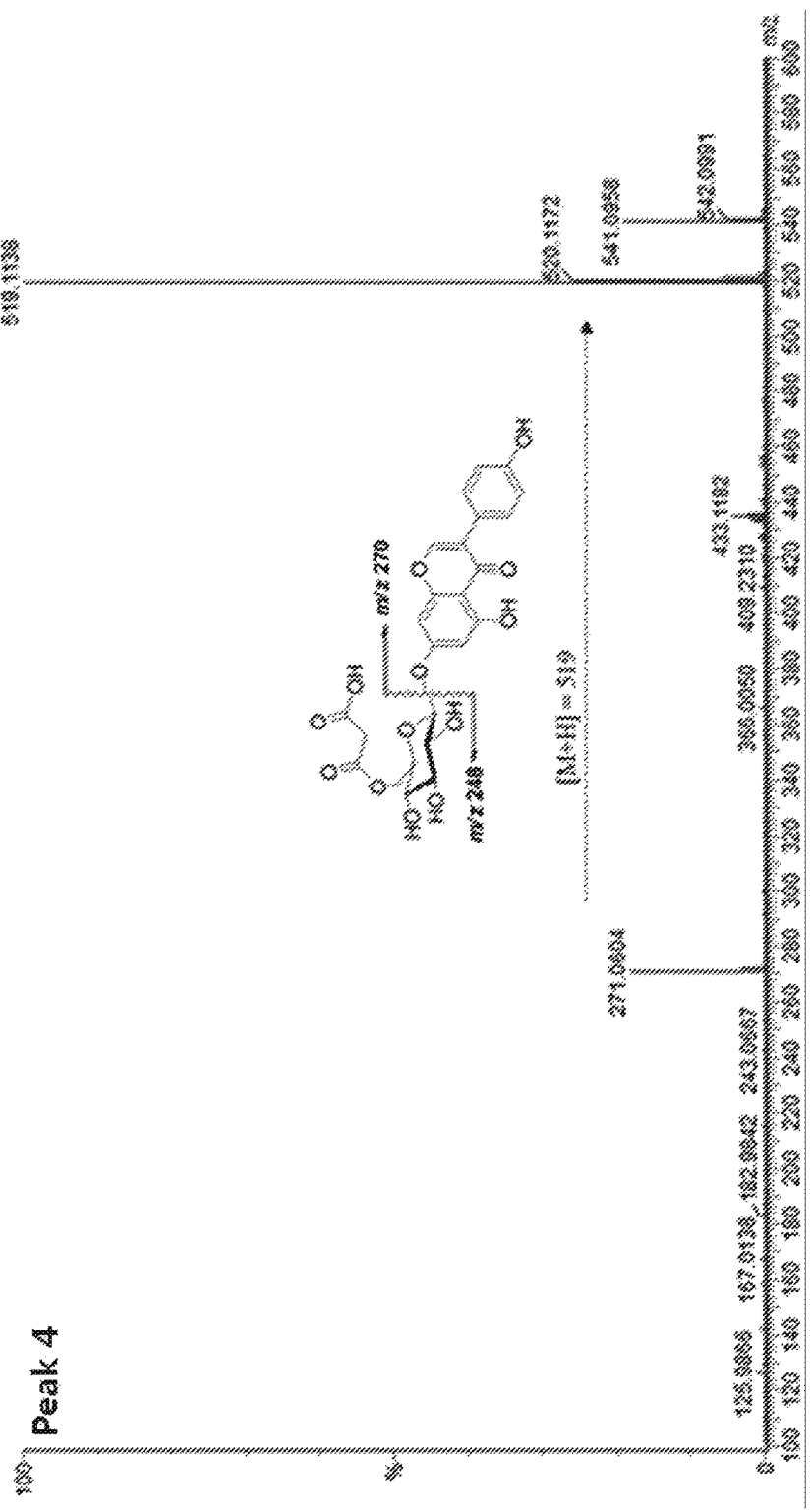
[Figure 7]

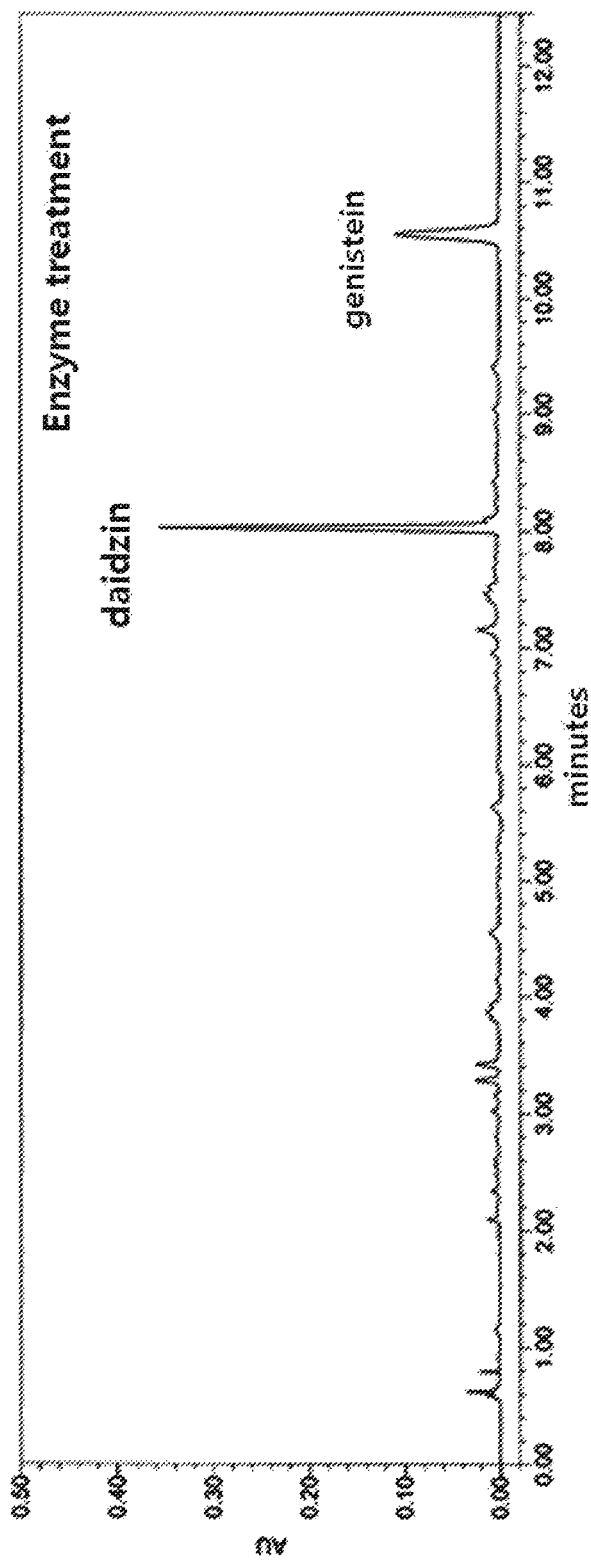
[Figure 8]

[Figure 9]
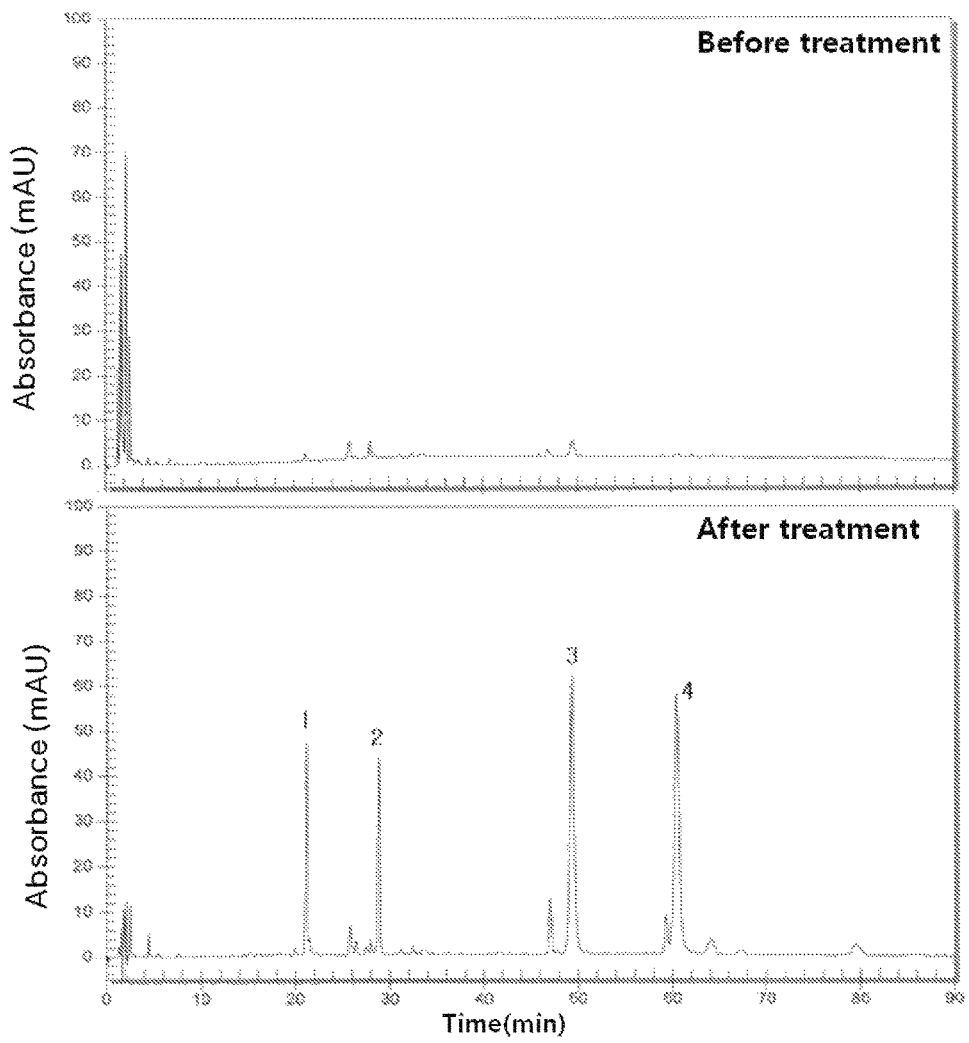

[Figure 10]
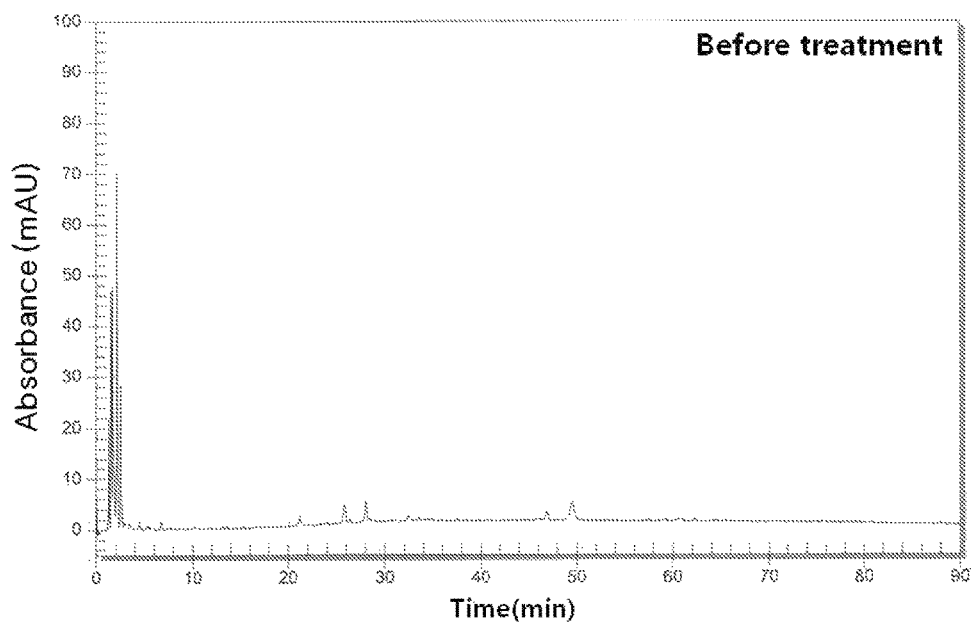

[Figure 11]
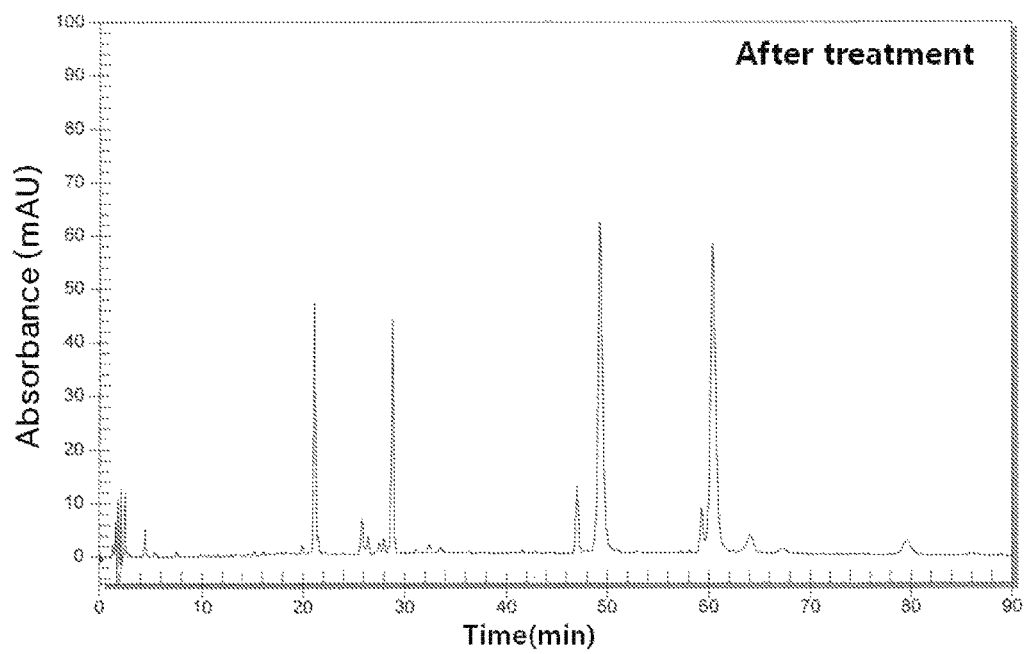

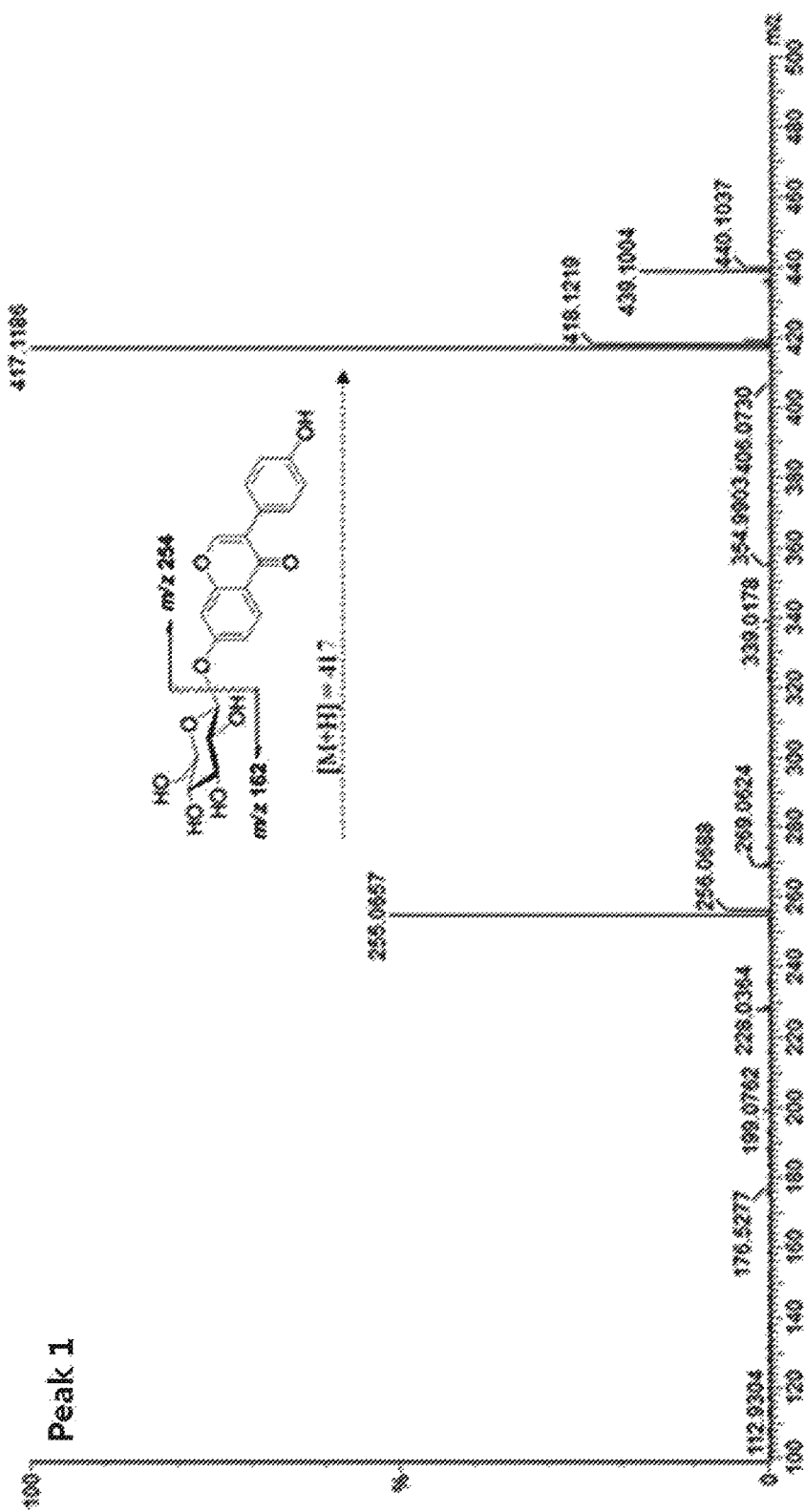

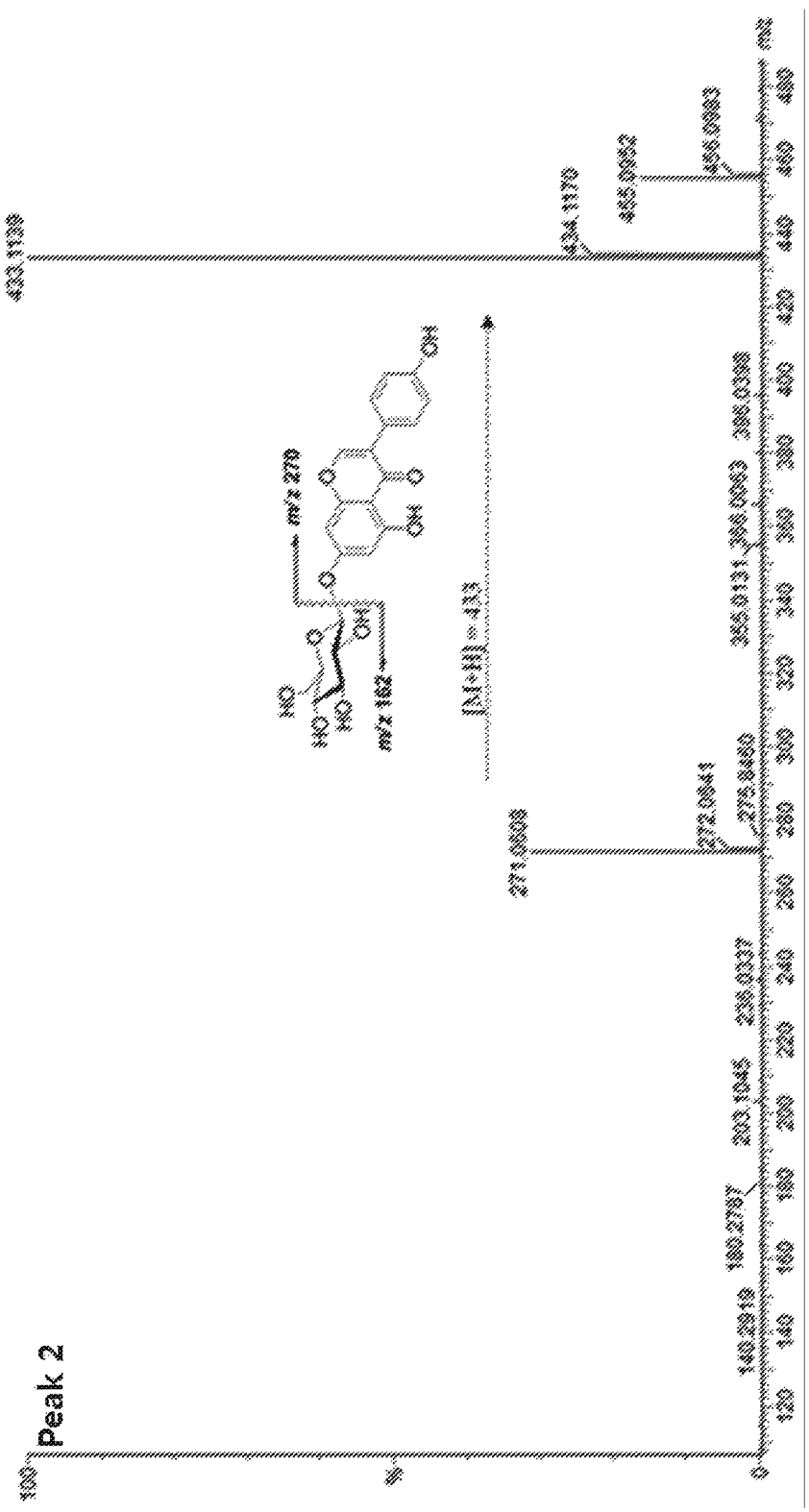
[Figure 13]

[Figure 14]
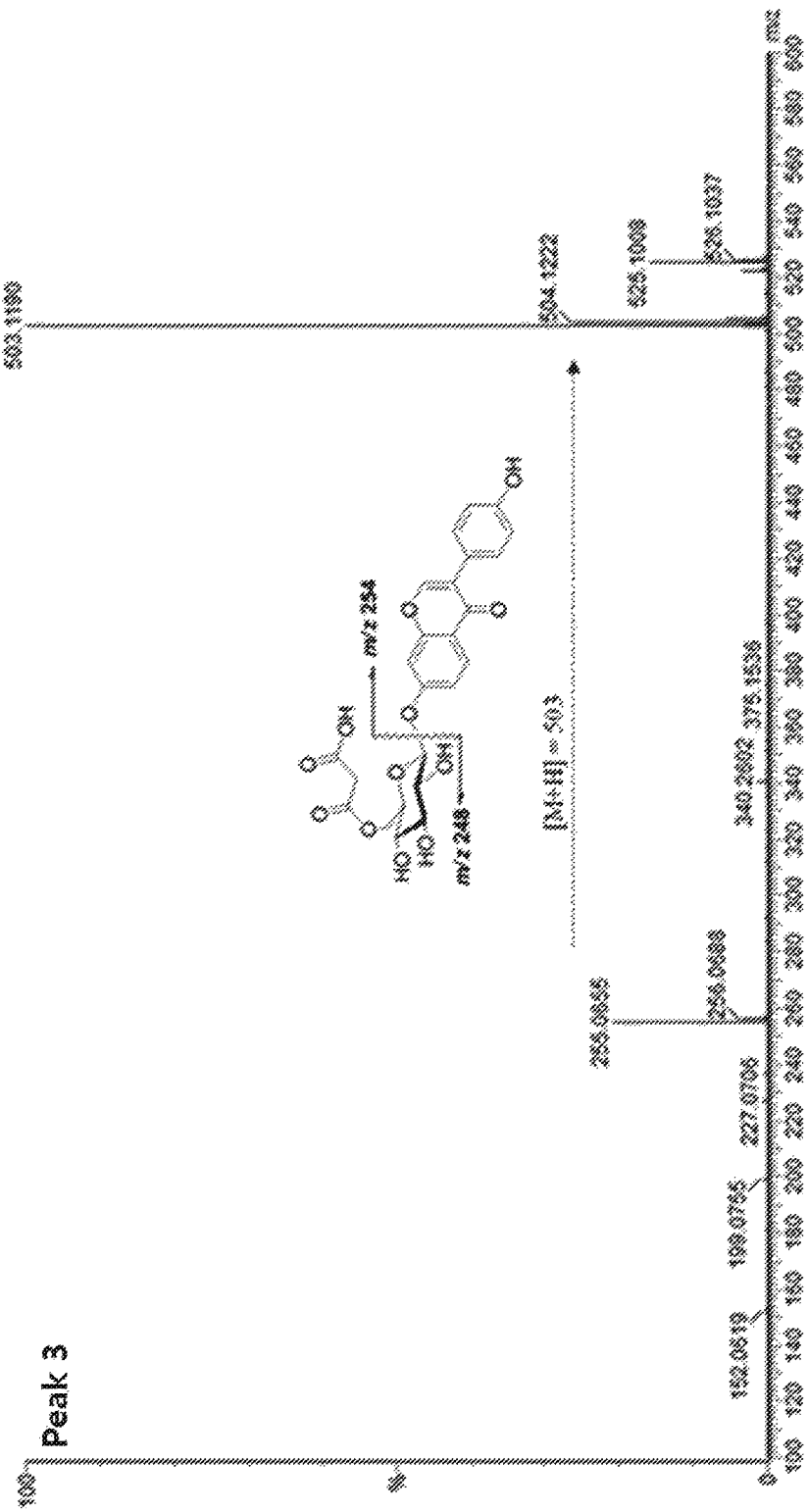

[Figure 15]
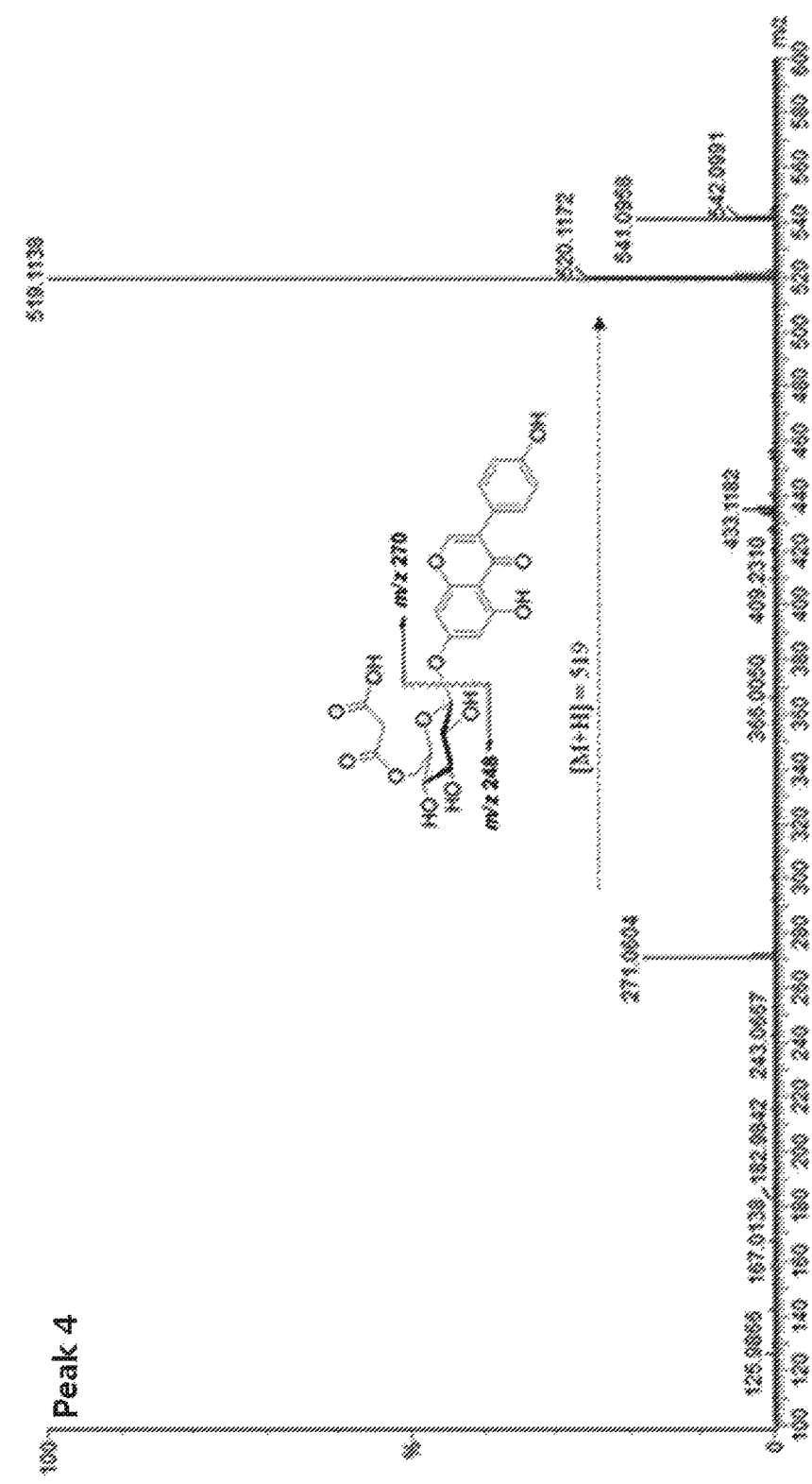

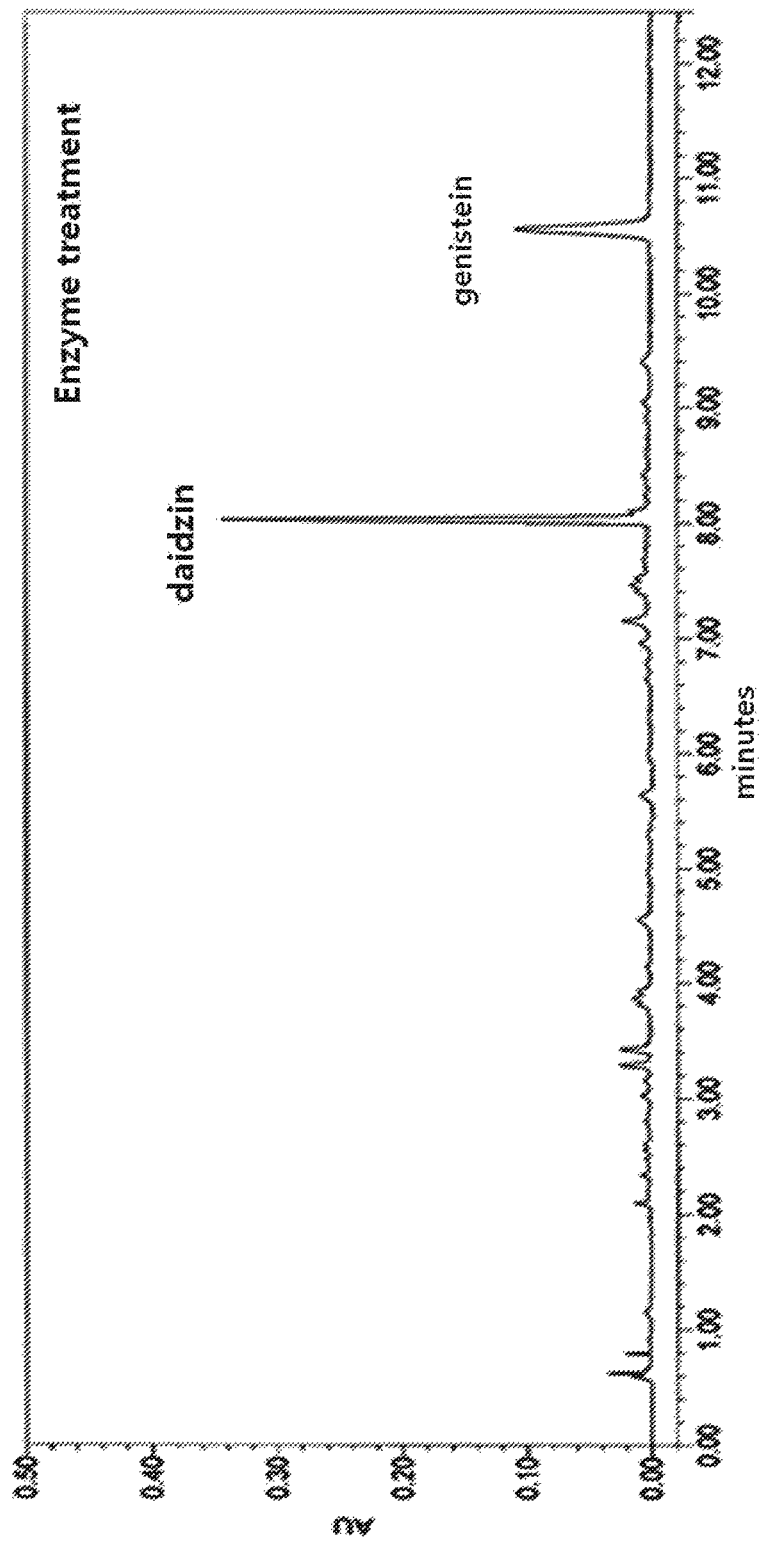

BEAN LEAVES OR BEAN STEMS HAVING HIGH ISOFLAVONE DERIVATIVES CONTENT AND METHOD FOR PREPARING SAME

CROSS REFERENCE TO RELATED APPLICATION

This patent application is a continuation of PCT/KR2014/011493, filed on Nov. 27, 2014, which claims the benefit of priority from Korean Patent Application No. 10-2013-0155430, filed on Dec. 13, 2013 and Korean Patent Application No. 10-2014-0082481 filed on Jul. 2, 2014. The contents of all three of these patent applications are incorporated herein by reference.

TECHNICAL FIELD

The present invention relates to a method for preparing soybean leaves or soybean stems having high isoflavone derivative content, the soybean leaves or soybean stems having high isoflavone derivative content prepared by the method, a use of the soybean leaves or soybean stems having high isoflavone derivative content, and a method for massively producing an isoflavone derivative from the soybean leaves or soybean stems.

BACKGROUND ART

An isoflavone derivative is a representative flavonoid having excellent pharmacological efficacy, and a lot of capital is investigated in the development of functional plants having high content of the isoflavone derivative. Since isoflavone has a chemically similar structure as non-steroid estrogen and has a similar physiological property as estrogen, isoflavone is referred to as phytoestrogen. Isoflavone has a similar structure as estrogen, i.e. female hormone, thereby showing useful bioactivity expected from estrogen. In particular, it has been reported that isoflavone reduces both the risk of osteoporosis after menopause, and plasma cholesterol. It has been also reported that isoflavone has an effect of reducing a risk of coronary heart diseases and has an excellent antioxidative activity.

Isoflavone is present in a glycoside form in which beta-glycoside is linked, or a non-glycoside from in which a sugar is removed. Examples of non-glycosides include genistein, daidzein and glycitein, and examples of glycosides include genistin, daidzin and glycitin. While unfermented foods derived from soybeans mostly include glycoside, fermented foods mostly include non-glycoside, because sugars are degraded from glycoside by the bacteria associated with fermentation.

Most isoflavone used as a food and medicinal material is extracted from soybeans and red clovers and used. Various breeding studies have been conducted to develop soybeans having high isoflavone content, but soybeans having isoflavone content of 4000 μg/g has been reported as the soybean having the highest level (see J. Agric. Food Chem. 2012, 60, 6045-6055). In addition, Korean Patent Publication 2003-93025 discloses a method of preparing germinating soybeans containing high concentration isoflavone by immersing washed soybeans in purified water, and then germinating them to increase isoflavone content by 40-70%. However, there is a drawback in that the isoflavone content is still low.

It has been reported that soybean leaves contain an extremely low amount of isoflavone derivatives. Specifically, soybean leaves contain daidzin (undetected), genistin (90 μg/g), malonyldaidzin (undetected), malonylgenistin (310 μg/g), aidzein (undetected), and genistein (undetected) (see BIOMEDICINE & PHARMACOTHERATY, 2002, 56, 289-295).

SUMMARY

As a result of trying to develop soybean leaves or soybean stems having high isoflavone derivative content, the present inventors have found that, when treated with ethylene or 2-chloroethylphosphonic acid (ethephon), i.e. an ethylene donor during cultivation of soybeans, high concentrations of isoflavone derivatives are accumulated in soybean leaves or soybean stems.

Disclosure of the Technical Problem

One object of the present invention is to provide a method for preparing soybean leaves or soybean stems having high isoflavone derivative content including treating soybean leaves or soybean stems with ethylene, an ethylene donor, or ethylene generator.

Another object of the present invention is to provide soybean leaves or soybean stems having high isoflavone derivative content prepared by the preparation method.

Still another object of the present invention is to provide a use of a food and a medicinal material including the soybean leaves or soybean stems having high isoflavone derivative content, an extract of the soybean leaves or soybean stems, or a fraction of the extract.

Even another object of the present invention is to provide a method for massively producing an isoflavone derivative from the soybean leaves or soybean stems by using ethylene, an ethylene donor, or an ethylene generator.

Technical Solution

In order to achieve the objects, the present invention provides a method for preparing soybean leaves or soybean stems having high isoflavone derivative content represented by the following [Formula 1], the method including treating soybean leaves or soybean stems with ethylene, an ethylene donor, or ethylene generator;

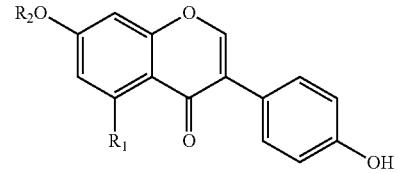

[Formula 1]

(wherein, $R_1$ independently is H or OH, and $R_2$ independently is H, glucose, or glucose malonate).

The present invention also provides soybean leaves or soybean stems having high isoflavone derivative content prepared by the preparation method.

Furthermore, the present invention provides a composition including soybean leaves or soybean stems having high isoflavone derivative content according to the present invention, an extract of the soybean leaves or soybean stems, or a fraction of the extract.

The present invention also provides a pharmaceutical composition for preventing and treating diseases due to estrogen deficiency, the composition containing, as an active ingredient, the soybean leaves or soybean stems having high isoflavone derivative content according to the present invention, the extract of the soybean leaves or soybean stems, or the fraction of the extract.

Furthermore, the present invention provides a health food for preventing and alleviating diseases due to estrogen deficiency, the composition containing, as an active ingredient, the soybean leaves or soybean stems having high isoflavone derivative content according to the present invention, the extract of the soybean leaves or soybean stems, or the fraction of the extract.

The present invention also provides a pharmaceutical composition for antioxidation, the composition containing, as an active ingredient, the soybean leaves or soybean stems having high isoflavone derivative content according to the present invention, the extract of the soybean leaves or soybean stems, or the fraction of the extract.

Furthermore, the present invention provides a health food for antioxidation, the food containing, as an active ingredient, the soybean leaves or soybean stems having high isoflavone derivative content according to the present invention, the extract of the soybean leaves or soybean stems, or the fraction of the extract.

The present invention also provides a pharmaceutical composition for skin care containing, as an active ingredient, the soybean leaves or soybean stems having high isoflavone derivative content according to the present invention, the extract of the soybean leaves or soybean stems, or the fraction of the extract.

Furthermore, the present invention provides a cosmetic composition for skin care containing, as an active ingredient, the soybean leaves or soybean stems having high isoflavone derivative content according to the present invention, the extract of the soybean leaves or soybean stems, or the fraction of the extract.

The present invention also provides a health food for skin care containing, as an active ingredient, the soybean leaves or soybean stems having high isoflavone derivative content according to the present invention, the extract of the soybean leaves or soybean stems, or the fraction of the extract.

Furthermore, the present invention provides tea using the soybean leaves or soybean stems having high isoflavone derivative content according to the present invention.

The present invention also provides a method for preparing tea using the soybean leaves or soybean stems having high isoflavone derivative content according to the present invention.

Furthermore, the present invention provides a method for massively producing an isoflavone derivative from soybean leaves or soybean stems by using ethylene, an ethylene donor or ethylene generator.

Further, the present invention provides a method for massively producing an isoflavone derivative including:

1) treating soybean leaves or soybean stems with ethylene, an ethylene donor, or ethylene generator to prepare soybean leaves or soybean stems; and 2) extracting the soybean leaves or soybean stems in step 1) and isolating the isoflavone derivative.

Advantageous Effects

The present invention has found that, when a soybean plant is treated with ethylene or ethephon, i.e. ethylene donor after 10-90 days of seeding, an isoflavone derivative is accumulated in soybean leaves or soybean stems in a high concentration. Therefore, as well as the method for preparing soybean leaves or soybean stems having high isoflavone derivative content, the soybean leaves or soybean stems having high isoflavone derivative content, the extract of the soybean leaves or soybean stems, and the fraction of the extract can be useful as medicinal materials and foods for diseases caused by estrogen imbalance and lack of antioxidative activity.

BRIEF DESCRIPTION OF THE DRAWINGS

FIG. 1 is a UPLC chromatogram showing a pattern of increase of isoflavone derivative content according to a cultivation period after soybean leaves are treated with ethephon.

FIG. 2 shows an UPLC chromatogram result of an extract obtained by extracting soybean leaves with ethanol before ethephon treatment.

FIG. 3 shows an UPLC chromatogram result of an extract obtained by extracting soybean leaves with ethanol 7 days after ethephon treatment.

FIG. 4 shows a mass spectrometry result (Q-TOF MS) verifying that peak 1 in FIG. 3 is daidzin.

FIG. 5 shows a mass spectrometry result (Q-TOF MS) verifying that peak 2 in FIG. 3 is genistin.

FIG. 6 shows a mass spectrometry result (Q-TOF MS) verifying that peak 3 in FIG. 3 is malonyldaidzin.

FIG. 7 shows a mass spectrometry result (Q-TOF MS) verifying that peak 4 in FIG. 3 is malonylgenistin.

FIG. 8 shows an UPLC chromatogram result of an extract obtained by extracting soybean leaves with ethanol 7 days after ethephon treatment and then treated with β-glucosidase.

FIG. 9 shows an HPLC chromatogram of patterns of increase in isoflavone derivative content before and after soybean stems are treated with ethylene.

FIG. 10 shows an HPLC chromatogram result of an extract obtained by extracting soybean stems with ethanol before ethylene treatment.

FIG. 11 shows an HPLC chromatogram result of an extract obtained by extracting soybean stems with ethanol after ethylene treatment.

FIG. 12 shows a mass spectrometry result (Q-TOF MS) verifying that peak 1 in FIG. 11 is daidzin.

FIG. 13 shows a mass spectrometry result (Q-TOF MS) verifying that peak 2 in FIG. 11 is genistin.

FIG. 14 shows a mass spectrometry result (Q-TOF MS) verifying that peak 3 in FIG. 11 is malonyldaidzin.

FIG. 15 shows a mass spectrometry result (Q-TOF MS) verifying that peak 4 in FIG. 11 is malonylgenistin.

FIG. 16 shows an UPLC chromatogram result of an extract obtained by extracting soybean stems with ethanol after ethylene treatment and then treated with β-glucosidase.

MODE FOR CARRYING OUT THE INVENTION

Hereinafter, the present invention will be described in more detail.

The present invention provides a method for preparing soybean leaves or soybean stems having high isoflavone derivative content, the method including treating soybean leaves or soybean stems with ethylene, an ethylene donor or ethylene generator.

The soybean leaves or soybean stems are preferably soybean leaves or soybean stems after 10 days or more of seeding, and more preferably after 40 days of seeding, but not limited thereto.

The ethylene donor is preferably ethephon, but not limited thereto. The ethylene is the simplest olefin-based hydrocarbon (Formula $C_2H_4$) and is colorless and sweet gas. A type of phytoestrogen promotes physiological changes of fruits after harvest, in particular mature of garden products or mature of plant tissue such as xanthism of green vegetables. In addition, the 2-chloroethylphosphonic acid (ethephon), which is one type of ethylene generators, is characterized by generating ethylene under the neutral and alkaline condition of pH 4.1 or more, and promoting mature, ripening or coloring by being degraded and generating ethylene when applying 1000-2000 times of solution in a liquid phase to fruits, and garden fruits.

The ethylene, ethylene donor, or ethylene generator is preferably treated in a concentration of 5 to 500 ppm, and more preferably a concentration of 5 to 100 ppm, but not limited thereto. The ethylene, ethylene donor, or ethylene generator may be treated before or after harvest of soybean leaves or soybean stems.

The isoflavone derivative is preferably a compound represented by the following [Formula 1], and more preferably any one of compounds represented by the following [Formula 2] to [Formula 7], but not limited thereto.

[Formula 1]

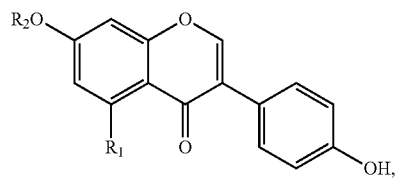

(wherein, $R_1$ independently is H or OH, and $R_2$ independently is H, glucose, or glucose malonate).

[Formula 2]

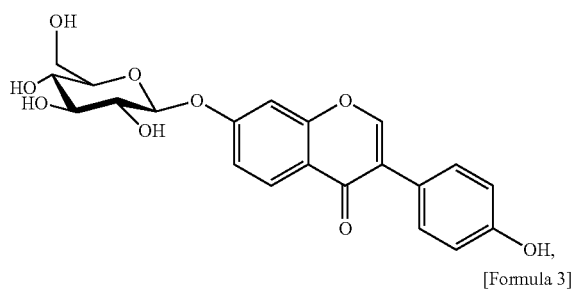

[Formula 3]

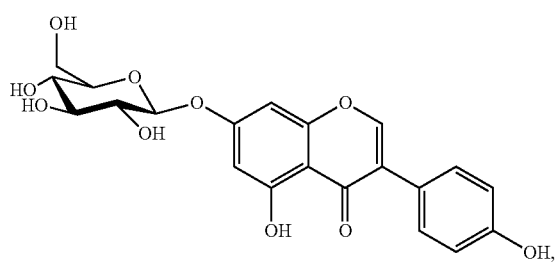

[Formula 4]

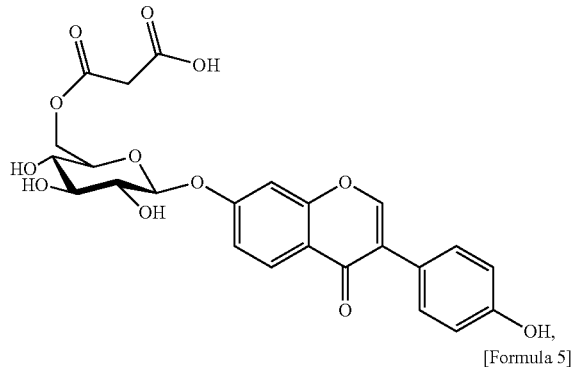

[Formula 5]

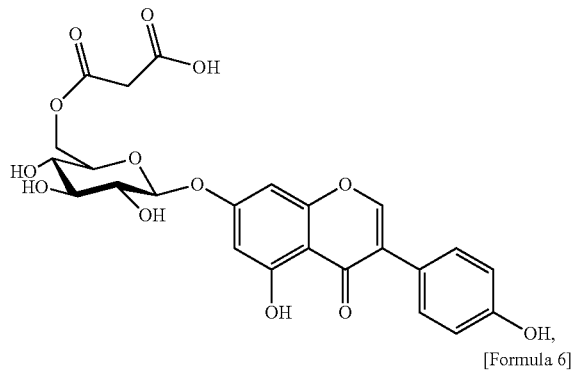

[Formula 6]

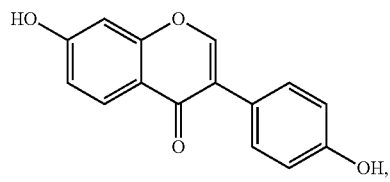

[Formula 7]

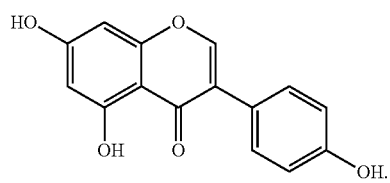

The present invention also provides soybean leaves or soybean stems having high isoflavone derivative content prepared by the preparation method.

The isoflavone derivative is preferably a compound represented by the following [Formula 1], and more preferably any one of compounds represented by the following [Formula 2] to [Formula 7], but not limited thereto.

In a particular embodiment of the present invention, the present inventors treat a soybean plant with ethephon diluted in water (5-100 ppm) after 40 days of soybean seeding (growth period R4). Consequently, it has been found that, from 1 day after the treatment, an isoflavone derivative is significantly increased and reached a maximum value after 5-12 days of the treatment (see FIG. 1). In addition, it has been found that soybean leaves without the ethephon treatment include, as main compounds, kaempferol glycoside, i.e., kaempferol-3-O-β-D-glucopyranosyl(1→2)-α-L-rhamnopyranosyl(1→6)-β-D-galactopyranoside, kaempferol-3-O-β-D-glucopyranosyl(1→2)-α-L-rhamnopyranosyl (1→6)-β-D-glucopyranoside, kaempferol-3-O-(2,6-di-O-α-L-rhamnopyranosyl)-β-D-glucopyranoside, kaempferol-3-O-β-digalactopyranoside, kaempferol-3-O-β-diglucopyranoside, kaempferol-3-O-α-L-rhamnopyranosyl (1→6)-β-D-galactopyranoside. However, it has been found that, in the soybean leaves treated with ethephon, 4 isoflavone derivatives, daidzin, genistin, malonyldaidzin, malonylgenistin are rapidly accumulated in the soybean leaves (see table 1). Further, the soybean leaves treated with ethephon are extracted with ethanol to obtain an extract. Then, the extract and the soybean leave extract are treated with β-glucosidase, and then isolation and purification is performed to obtain 6 isoflavone derivatives, daidzin, genistin, malonyldaidzin, malonylgenistin, daidzein, and genistein (see FIGS. 3 to 8).

Additionally, the present inventors conduct quantitative analysis on the four isoflavone derivatives, daidzin, genistin, malonyldaidzin, and malonylgenistin respectively isolated from soybean leaves harvested after ethephon treatment and soybean leaves treated with ethephon after harvest. Consequently, it has been found that, for the soybean leaves harvested after ethephon treatment, isoflavone derivative content is significantly increased, and for the soybean leaves treated with ethephon after harvest, isoflavone derivative content is also significantly increased. Therefore, it has been found that both methods of harvesting soybean leaves after ethephon treatment and treating harvested soybean leaves with ethephon are available as a method for preparing bean leaves having high isoflavone derivative content (see tables 1 and 2).

Further, the present inventors have found that, when treating a soybean plant with ethylene (100-1000 ppm) after 40 days of soybean seeding (growth period R4), the isoflavone derivative is significantly increased in soybean stems after the treatment relative to before treatment (see FIG. 9). Moreover, the isoflavone derivative is not detected in soybean stems without ethylene treatment. However, it has been found that, in the soybean stems treated with ethylene, four isoflavone derivatives, daidzin, genistin, malonyldaidzin, and malonylgenistin are rapidly accumulated in the soybean stems (see table 3). Further, the soybean stems treated with ethylene are extracted with ethanol to obtain an extract. Then, soybean stem extract is treated with β-glucosidase, and then isolation and purification is performed to obtain 6 isoflavone derivatives, daidzin, genistin, malonyldaidzin, malonylgenistin, daidzein, and genistein (see FIGS. 11 to 16).

Additionally, the present inventors conduct quantitative analysis on the four isoflavone derivatives, daidzin, genistin, malonyldaidzin, and malonylgenistin respectively isolated from soybean stems harvested after ethylene treatment and soybean stems treated with ethylene after harvest. Consequently, it has been found that, for the soybean stems harvested after ethylene treatment, isoflavone derivative content is significantly increased. Therefore, it has been found that the method of harvesting soybean stems after ethylene treatment is available as a method for preparing soybean stems having high isoflavone derivative content (see table 2).

Further, the present invention provides a method for massively producing an isoflavone derivative from soybean leaves or soybean stems by using ethylene, an ethylene donor, or ethylene generator.

Specifically, the method preferably includes:
1) treating soybean leaves or soybean stems with ethylene, an ethylene donor, or ethylene generator to prepare soybean leaves or soybean stems; and 2) extracting the soybean leaves or soybean stems in step 1) and isolating the isoflavone derivative.

In the method, the soybean leaves or soybean stems in step 1) are preferably soybean leaves or soybean stems after 10 days or more of seeding, more preferably after 40 days of seeding, and most preferably after 10 to 90 days of seeding.

In the method, the ethylene, ethylene donor, or ethylene generator in step 1) may be treated before or after harvest of soybean leaves.

In the method, the ethylene donor in step 1) is preferably ethephon, but not limited thereto, and all materials inducing or generating ethylene are available.

In the method the ethylene, ethylene donor, or ethylene generator in step 1) is preferably treated in a concentration of 5 to 1000 ppm, more preferably 5 to 500 ppm, and most preferably 5 to 100 ppm.

In the present invention, the isoflavone derivative is preferably a compound represented by [Formula 1] above, and more preferably any one or more compounds represented by [Formula 2] to [Formula 7] above.

In the present invention, soybean leaves or soybean stems are treated with ethylene and ethephon, i.e. ethylene donor, to prepare soybean leaves or soybean stems having high isoflavone derivative content. Also, the preparation method may be useful as a method for massively producing the isoflavone derivative. In addition, by finding that both methods of harvesting soybean leaves or soybean stems after ethephon treatment and treating soybean leaves or soybean stems with ethephon after harvest show significantly increased isoflavone derivative content, the method of preparing soybean leaves or soybean stems having high isoflavone derivative content by treating soybean leaves or soybean stems with ethylene and an ethylene donor before or after harvest may be used as a method for massively producing an isoflavone derivative.

Further, the present invention provides a composition including soybean leaves or soybean stems having high isoflavone derivative content, an extract of the soybean leaves or soybean stems, or a fraction of the extract, wherein the soybean leaves or soybean stems are prepared by treating soybean leaves or soybean stems with ethylene, an ethylene donor or ethylene generator.

The extract the soybean leaves or soybean stems or the fraction thereof is preferably prepared by the preparation method including the following step, but not limited thereto:
1) adding an extraction solution to the soybean leaves or soybean stems for extraction;
2) filtering the extract of step 1);
3) concentrating the filtered extract in step 2) under reduced pressure, and then drying the resultant to prepare soybean leaves or soybean stems; and
4) additionally extracting the soybean leaves or soybean stems in step 3) with an organic solvent to prepare the fraction of soybean leaves or soybean stems.

In the method, the soybeans leaves or soybean stems in step 1) are taken from soybean plants in which isoflavone is accumulated in a high concentration after ethylene or ethephon treatment, and then used. Although the ethylene or ethephon treatment is available after the plant is harvested, it is preferable that the treatment be performed before the harvest. All of leaves, stems, or roots of the soybean plants treated with ethylene or ethephon are available. According to a preferred embodiment of the present invention, soybean leaves or soybean stems are preferably used, but not limited thereto.

In the method, the extraction solvent in step 1) is preferably water, alcohol, or a mixture thereof. As the alcohol, $C_1$ to $C_4$ low grade alcohol is preferably used. As the low grade alcohol, ethanol or methanol is preferably used. As an extraction method, shaking extraction, soxhlet extraction, or reflux extraction is preferably used, but not limited thereto. The extraction solvent is preferably added for extraction in an amount of 1 to 10 times, and more preferably 4 to 6 times of the amount of dried soybean leaves or soybean stems. The extraction temperature is preferably 20° C. to 100° C., more preferably 20° C. to 40° C., and most preferably room temperature, but not limited thereto. The extraction time is preferably 10 to 48 hours, more preferably 15 to 30 times, and most preferably 24 hours, but not limited thereto. Furthermore, the extraction number is preferably 1 to 5 times, more preferably 3 to 4 times, and most preferably 3 times, but not limited thereto.

In the method, reduced pressure concentration in step 3) preferably employs a vacuum reduced pressure concentrator, or rotary vacuum evaporator, but not limited thereto. In addition, the drying is preferably reduced pressure drying, vacuum drying, boiling drying, spray drying or freeze drying, but not limited thereto.

In the method, the soybean leave or soybean stem extract in step 4) is preferably a dark brown crude extract which is a soybean stem extract concentrated under reduced pressure, but not limited thereto. Also, the organic solvent is preferably n-hexane, chloroform, ethyl acetate or butanol. According to a preferred embodiment of the present invention, chloroform is more preferably used, but not limited thereto. The fraction is preferably an n-hexane fraction, chloroform fraction, ethylacetate fraction, butanol fraction or water fraction obtained by suspending the soybean leave or soybean stem extract in water and then sequentially fractionating the suspension with n-hexane, chloroform, ethyl acetate, butanol, and water, but not limited thereto. The fraction may be obtained by repetitively performing the fractionation process from the soybean leave or soybean stem extract for 1 to 5 times, preferably 3 times. Also, the reduced pressure concentration is preferably performed after fractionation, but not limited thereto.

Also, the present invention provides a pharmaceutical composition for treating and preventing diseases due to estrogen deficiency, the composition containing, as an active ingredient, soybean leaves or soybean stems having high isoflavone derivative content prepared by treating the soybean leaves or soybean stems with ethylene, an ethylene donor, or ethylene generator, an extract of the soybean leaves or soybean stems, or a fraction of the extract.

The disease due to estrogen deficiency is preferably any one disease selected from the group consisting of osteoporosis, heart diseases, breast cancer, vaginal diseases, hyperlipidemia, skin aging and facial blushing, but not limited thereto.

Since the isoflavone derivatives isolated from the soybean leaves or soybean stems having high isoflavone content have established bioactivity, the extract of the soybean leaves or soybean stems including these compounds and the fraction thereof may be useful as a pharmaceutical composition for treating and preventing diseases due to estrogen deficiency.

The composition of the present invention may further include an appropriate carrier, excipient, and diluent typically used in the preparation of pharmaceutical compositions.

The composition of the present invention may be orally or parenterally administered. For parenteral administration, topical skin, intraperitoneal injection, rectal injection, subcutaneous injection, intravenous injection, intramuscular injection, or intrathoracic injection infusion method is preferably selected, but not limited thereto.

The composition of the present invention may be formulated as an oral formulation, topical formulation, suppository and sterilized injectable solution such as powder, granules, tablets, capsules, suspension, emulsion, syrup, and aerosol according to the typical method, and then used. Examples of the carrier, excipient, and diluent included in the composition may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil. For formulation, a typically used diluent or excipient such as a filling agent, a bulking agent, a binding agent, a wetting agent, a disintegrating agent, a surfactant and the like is used for preparation. The solid formulation for oral administration includes a tablet, bolus, powder, granule, and capsule, etc. The solid formulation is prepared by mixing at least one excipient such as starch, calcium carbonate, sucrose, lactose or gelatin in a mixed herb medicine. In addition to the simple excipient, a lubricant such as magnesium stearate and talc is used. Examples of liquid formulation for oral include suspension, liquid for internal use, emulsion and syrup. In addition to the typically used simple diluent such as water and liquid paraffin, various excipients such as wetting agents, sweetening agents, flavoring agents, and preservants may be included. Examples of the formulations for parenteral administration includes sterilized solution, non-aqueous solvent, suspension, emulsion, lyophilized formulation, and suppository. As the non-aqueous solvent and suspension, propylene glycol, polyethylene glycol, vegetable oil such as olive oil, and injectable ester such as ethyl oleate may be used. As a base of the suppository, witepsol, macrogol, tween 61, cacao butter, laurin butter, and glycerogelatin may be used.

A preferred administration dose of the composition of the present invention varies depending on the state and weight of patients, severity of diseases, formations of drugs, and administration routes and periods, and will be selected by a person skilled in the art as appropriate. However, for the desired effect, the composition is preferably administered in a dose of 0.0001 to 1 g/kg, and preferably 0.001 to 200 mg/kg per day, but not limited thereto. The administration may be performed once a day, or be divided into several times. The administration dose does not limit the scope of the present invention in any ways.

Further, the present invention provides a health food for preventing and alleviating diseases due to estrogen deficiency, the food containing, as an active ingredient, soybean leaves or soybean stems having high isoflavone derivative content prepared by treating soybean leave or soybean stems with ethylene, an ethylene donor, or ethylene generator, an extract of the soybean leaves or soybean stem, or a fraction of the extract.

The disease due to estrogen deficiency is preferably any one disease selected from the group consisting of osteoporosis, heart diseases, breast cancer, vaginal diseases, hyperlipidemia, skin aging and facial blushing.

Since the isoflavone derivatives isolated from the soybean leaves or soybean stems having high isoflavone content of the present invention have established bioactivity, the extract of the soybean leaves or soybean stems including these compounds and the fraction thereof may be useful as a health food for alleviating and preventing diseases due to estrogen deficiency.

In the health food of the present invention, the soybean leaves or soybean stems having high isoflavone derivative content, the extract of the soybean leaves or soybean stems, or the fraction thereof may be intactly added, or used with other foods or food ingredients as appropriate according to the typical method.

Types of the foods are not particularly limited. Examples of the foods include functional mixed tea, drinks, meats, sausage, bread, biscuits, rice cake, chocolate, candies, snacks, cookies, pizzas, ramen, other noodles, gums, dairy products including ice cream, various soup, beverage, alcohol drinks and vitamin complex, and the foods also include all health foods in the common sense.

The soybean leaves or soybean stems having high isoflavone derivative content according to the present invention, the extract of the soybean leaves or soybean stems, or fraction of the extract may be intactly added to the food or used with other foods or food ingredients as appropriately according to the typical method. A mixed amount of the active ingredient may be appropriately determined according to the use thereof (i.e., prevention or alleviation). Generally, the amount of the soybean leaves or soybean stems having high isoflavone derivative content, the extract of the soybean leaves or soybean stems, or the fraction of the extract in the health food may be 0.01 to 15 weight with respect to the total weight of the foods, and 0.02 to 5 g, preferably 0.3 to 1 g was added based on 100 ml of the health beverage composition. However, for long term administration for the purpose of health and hygiene or the purpose of health control, the amount may be less than or equal to the above range. Also, since there is no problem in safety, the active ingredient may be used in an amount equal to or more than the above range.

Except that the health functional beverage composition of the present invention contains, as an essential ingredient, soybean leaves or soybean stems having high isoflavone derivative content, the extract of the soybean leaves or soybean stems or the fraction of the extract in a predetermined ratio, other ingredients are not particularly limited. Also, various flavoring agents or natural carbohydrates may be included as additional ingredients as typical beverages. Examples of the natural carbohydrate described above include: typical sugars such as monosaccharide, for example glucose, and fructose; disaccharide, for example maltose, and sucrose; and polysaccharide, for example dextrin, and cyclodextrin and sugar alcohol such as xylitol, sorbitol, and erythritol. As a flavoring agent in addition to those described above, a natural flavoring agent (thaumatin, stevia extract, for example, rebaudioside A, and glycyrrhizin) and synthetic flavoring agent (saccharin, aspartame) may be advantageously used.

In addition to those described above, the food of the present invention may contain various nutrients, vitamins, minerals (electrolyte), flavoring agents such as synthetic flavoring agents and natural flavoring agents, coloring agents and enhancers (cheese, chocolate, etc.), pectic acids and a salt thereof, alginic acids and a salt thereof, organic acids, protective colloid thickening agents, pH adjusters, stabilizers, preservatives, glycerin, alcohol, carbonating agent used in carbonated drinks, etc. In addition, the soybean leaves or soybean stems having high isoflavone derivative content of the present invention, the extract of the soybean leaves or soybean stems, or the fraction of the extract may contain fruit flesh for preparation of natural fruit juice, fruit juice beverage and vegetable beverage. These ingredients are may be independently used or used in combination. The ratio of these additives is not important, and is generally selected in a range from 0 to about 20 parts by weight per 100 parts by weight of the soybean leaves or soybean stems having high isoflavone derivative content of the present invention, the extract of the soybean leaves or soybean stems, or the fraction of the extract.

Further, the present invention provides a pharmaceutical composition for antioxidation containing, as an active ingredient, soybean leaves or soybean stems having high isoflavone derivative content prepared by treating soybean leaves or soybean stems with ethylene, an ethylene donor, or ethylene generator, an extract of the soybean leaves or soybean stems, or a fraction of the extract.

Further, the present invention provides a health food for antioxidation containing, as an active ingredient, soybean leaves or soybean stems having high isoflavone derivative content prepared by treating soybean leaves or soybean stems with ethylene, an ethylene donor, or ethylene generator, an extract of the soybean leaves or soybean stems, or a fraction of the extract.

Since the isoflavone derivatives isolated from the soybean leaves or soybean stems having high isoflavone content of the present invention have established bioactivity, the extract of the soybean leaves or soybean stems including these compounds and the fraction thereof may be useful as a composition for antioxidation. Further, the present invention provides a pharmaceutical composition for skin care, containing, as an active ingredient, soybean leaves or soybean stems having high isoflavone derivative content prepared by treating soybean leaves or soybean stems with ethylene, an ethylene donor, or ethylene generator, an extract of the soybean leaves or soybean stems, or a fraction of the extract.

In addition, the present invention provides a cosmetic composition for skin care, containing, as an active ingredient, soybean leaves or soybean stems having high isoflavone derivative content prepared by treating soybean leaves or soybean stems with ethylene, an ethylene donor, or ethylene generator, an extract of the soybean leaves or soybean stems, or a fraction of the extract.

Further, the present invention provides a health food for skin care, containing, as an active ingredient, soybean leaves or soybean stems having high isoflavone derivative content prepared by treating soybean leaves or soybean stems with ethylene, an ethylene donor, or ethylene generator, an extract of the soybean leaves or soybean stems, or a fraction of the extract.

Since the isoflavone derivatives isolated from the soybean leaves or soybean stems having high isoflavone content of the present invention have established bioactivity, the extract of the soybean leaves or soybean stems including these compounds and the fraction thereof may be useful as a composition for skin care.

The cosmetic composition may be lotion, ointment, gel, cream, patch, or spray, but not limited thereto. In the preparation of the cosmetic composition containing soybean leaves or soybean stems having high isoflavone derivative content of the present invention, the extract of the soybean leaves or soybean stems, or the fraction of the extract, the soybean leaves or soybean stems having high isoflavone derivative content of the present invention, the extract of the soybean leaves or soybean stems, or the fraction of the extract may be added in 3 to 30 parts by weight, and preferably 5 to 20 parts by weight to the topical skin compositions typically included.

In addition to the soybean leaves or soybean stems having high isoflavone derivative content of the present invention, the extract of the soybean leaves or soybean stems, or the fraction of the extract, the cosmetic composition of the present invention may contain a supplement, which is typically used in the dermatological field, such as a fat material, an organic solvent, a solvent, a concentration agent, a gellating agent, a softener, an antioxidative agent, a suspending agent, a stabilizer, a foaming agent, perfume, a surfactant, water, an ionic or non-ionic emulsifier, a filling agent, a metal ion blocking agent, a chelating agent, a preservant, a vitamin, a blocking agent, a wetting agent, essential oil, a dye, a pigment, a hydrophilic or lipophilic active agent, lipid vesicle or any other ingredients typically used in the cosmetic composition.

Also, these ingredients may be introduced in an amount generally used in the dermatological field.

Further, the present invention provides tea using soybean leaves or soybean stems having high isoflavone derivative content according to the present invention.

Additionally, the present invention provides a mixed tea in which soybean leaves, or soybean stems having high isoflavone derivative content according to the present invention and an herb plant having flavor are mixed.

The tea using the soybean leaves or soybean stems may be prepared by the preparation method including:

1) washing and pulverizing the soybean leaves or soybean stems having high isoflavone derivative content according to the present invention;
2) roasting the pulverized soybean leaves or stems; and
3) drying the roasted soybean leaves or stems.

In the method, the pulverization in step 1) is preferably performed by using a pulverizer such that the size becomes 1 to 5 mm, but the size is not limited thereto.

In the method, the roasting in step 2) is preferably performed at a temperature of 250 to 300° C. for 30 to 60 minutes such that the soybean leaves or stems are not burned. However, the temperature and time are not limited thereto.

In the method, the drying in step 3) may be natural drying or be performed by using a drier. The drying is preferably performed at a temperature of 30 to 50° C. for 24 to 36 hours, but the temperature and time are not limited thereto.

The herb plant is preferably at least one selected from the group consisting of chamomile, lemon grass, rose hip, lavender, peppermint, fennel, rosemary, jasmine, hibiscus, rose flower, apple fruit, strawberry fruit, lemon fruit and orange flower. All herbs used as tea are available.

The tea or mixed tea may be processed in a form selected from the group consisting of flavored tea, tea bag, instant team and can.

Further, the present invention provides a method for treating and preventing diseases due to estrogen deficiency including administering, to a subject, the soybean leaves or soybean stems having high isoflavone derivative content of the present invention, the extract of the soybean leaves or soybean stems, or the fraction of the extract.

The present invention also provides an antioxidation method including administering, to a subject, the soybean leaves or soybean stems having high isoflavone derivative content of the present invention, the extract of the soybean leaves or soybean stems, or the fraction of the extract.

Further, the present invention provides a skin care method including administering, to a subject, the soybean leaves or soybean stems having high isoflavone derivative content of the present invention, the extract of the soybean leaves or soybean stems, or the fraction of the extract.

The present invention also provides the soybean leaves or soybean stems having high isoflavone derivative content of the present invention, the extract of the soybean leaves or soybean stems, or the fraction of the extract to be used as a pharmaceutical composition for preventing and treating diseases due to estrogen deficiency.

Further, the present invention provides the soybean leaves or soybean stems having high isoflavone derivative content of the present invention, the extract of the soybean leaves or soybean stems, or the fraction of the extract to be used as a health food for preventing and alleviating diseases due to estrogen deficiency.

The present invention also provides the soybean leaves or soybean stems having high isoflavone derivative content of the present invention, the extract of the soybean leaves or soybean stems, or the fraction of the extract to be used as a pharmaceutical composition for antioxidation.

Further, the present invention provides the soybean leaves or soybean stems having high isoflavone derivative content of the present invention, the extract of the soybean leaves or soybean stems, or the fraction of the extract to be used as a health food for antioxidation.

The present invention also provides the soybean leaves or soybean stems having high isoflavone derivative content of the present invention, the extract of the soybean leaves or soybean stems, or the fraction of the extract to be used as a pharmaceutical composition for skin care.

Further, the present invention provides the soybean leaves or soybean stems having high isoflavone derivative content of the present invention, the extract of the soybean leaves or soybean stems, or the fraction of the extract to be used as a cosmetic composition for skin care.

The present invention also provides the soybean leaves or soybean stems having high isoflavone derivative content of the present invention, the extract of the soybean leaves or soybean stems, or the fraction of the extract to be used as a health food for skin care.

Further, the present invention provides the soybean leaves or soybean stems having high isoflavone derivative content of the present invention, the extract of the soybean leaves or soybean stems, or the fraction of the extract to be used as tea.

Hereinafter, the present invention will be described in more detailed with reference to the following examples.

However, the following examples are only to illustrate the present invention, and the scope of the present invention is not limited thereto.

EXAMPLE 1

Preparation of Soybean Leaves and Soybean Stems Having High Isoflavone Derivative Content <1-1> Preparation of Soybean Leaves Having High Isoflavone Derivative Content Soybean seeds (*Glycine max*) were provided from Rural Development Administration and cultivated. Soybean plants were treated with 5-100 ppm of 2-chloroethylphosphonic acid (ethephon) or 5-500 ppm of ethylene after 10 to 90 days of seeding to prepare soybean leaves having high isoflavone content. A pattern of accumulation of isoflavone in soybean leaves may vary depending on the concentration of treated ethephon or ethylene and growth period of the treated plant.

Specifically, after 40 days of seeding, soybean plants were periodically treated with ethephon diluted in water to concentration of 50 ppm. Consequently, targeted isoflavone was rapidly accumulated after one day of the treatment. After 5-12 days of the treatment, soybean leaves in which the highest concentration of isoflavone was accumulated were achieved.

Additionally, soybean leaves were harvested from soybean plants (after 10-90 days) after seeding, and periodically treated with ethephon diluted to a concentration of 5-100 ppm. After 3-10 days of the treatment, soybean leaves in which the highest level of isoflavone derivative was accumulated were achieved.

Consequently, as shown in FIG. 1, the concentration of the target isoflavone derivative of soybean leaves was increased after the treatment. After 5-12 days of the treatment, soybean leaves in which the highest concentration of isoflavone derivative was accumulated were achieved. Also, it has been found that the soybean leaves gradually became yellow by the influence of ethylene which is an aging hormone in plants (FIG. 1). Consequently, from the result, isoflavone was accumulated in soybean leaves from the first day of treating soybean plants after 10 to 90 days of seeding with ethephon diluted to the degree of 5-100 ppm or 5-500 ppm ethylene, and soybean leaves having the highest level of isoflavone derivative content were achieved after 5-12 days of the treatment.

<1-2> Preparation of Soybean Stems Having Highest Isoflavone Derivative

Soybean seeds (*Glycine max*) were provided from Rural Development Administration and cultivated. Soybean plants were treated with 5-100 ppm of 2-chloroethylphosphonic acid (ethephon) or 100-1000 ppm of ethylene after 10 to 90 days of seeding to prepare soybean stems having high isoflavone content. A pattern of accumulation of isoflavone in soybean stems may vary depending on the concentration of treated ethephon or ethylene and growth period of the treated plant.

Specifically, after 40 days of seeding, soybean plants were periodically treated with 200 ppm of ethylene.

Consequently, as shown in FIG. 9, the concentration of the target isoflavone derivative of soybean stems was increased after the treatment. Also, it has been found that the soybean stems gradually became yellow by the influence of ethylene which is an aging hormone in plants (FIG. 9). Consequently, from the result, soybean stems in which isoflavone derivative content was rapidly accumulated were achieved after treating soybean plants after 10 to 90 days of seeding with ethephon diluted to a degree of 5-100 ppm or 100-1000 ppm of ethylene.

EXAMPLE 2

Preparation of Soybean Leaves and Soybean Stems Having High Isoflavone Derivative Content <2-1> Preparation of Soybean Leaves Having High Isoflavone Derivative Content Soybean leaves obtained through the method in Example <1-1> were dried and extracted with 50-100% alcohol for 3-10 days under 20-100° C. condition. The extracted solvent was concentrated under reduced pressure to obtain an extract with 8-15% yield.

Specifically, soybean leaves obtained through the method described in Example <1-1> were dried. Then, the 1 kg of the dried soybean leaves were extracted with 80% ethanol for 7 days at room temperature. Thereafter, the extracted solvent was concentrated under reduced pressure to obtain 86 g of the extract. Also, the dried soybean leaves were extracted with purified water under 40-100° C. condition. The extracted solvent was concentrated under reduced pressure to obtain an extract with 10-17% yield.

Consequently, as shown in FIGS. 2 and 3, it has been found that, when compared to the extract in which soybean leaves were extracted with ethanol before ethephon treatment, the extract in which soybean leaves were extracted with ethanol after 7 days of the ethephon treatment showed a significantly higher isoflavone derivative content (FIGS. 2 and 3).

<2-2> Preparation of Soybean Stems Having High Isoflavone Derivative Content

Soybean stems obtained through the method in Example <1-2> were dried and extracted with 50-100% alcohol for 3-10 days under 20-100° C. condition. The extracted solvent was concentrated under reduced pressure to obtain an extract with 8-15% yield.

Specifically, soybean stems obtained through the method described in Example <1-2> were dried. Then, 1 kg of the dried soybean stems were extracted with 80% ethanol for 7 days at room temperature. Thereafter, the extracted solvent was concentrated under reduced pressure to obtain 86 g of an extract. Also, the dried soybean stems were extracted with purified water under 40-100° C. condition. The extracted solvent was concentrated under reduced pressure to obtain an extract with 10-17% yield.

Consequently, as shown in FIGS. 10 and 11, it has been found that, when compared to the extract in which soybean stems were extracted with ethanol before ethylene treatment, the extract in which soybean stems treated with ethylene were extracted with ethanol showed significantly higher isoflavone derivative content (FIGS. 10 and 11).

EXAMPLE 3

Isolation and Purification of Isoflavone Derivative from Soybean Leaves and Soybean Stems <3-1> Isolation and Purification of Isoflavone Derivative from Soybean Leaves Isolation and purification of the isoflavone derivative in the ethanol fraction of soybean leaves having high isoflavone content obtained through the method described in Example <2-1> was performed by using MPLC (Teledyne Isco CombiFlash Companion). As a column material, C18 silica gel (YMC, 50 μm) was used. As an elution condition, water/acetonitrile mixed solution was used such that gradient elution in which acetonitrile solvent is increased from 0-90% was applied. As a result, four isoflavone derivatives were respectively isolated.

Further, the ethanol extract of soybean leaves having high isoflavone derivative content obtained through the method described in Example <2-1> was treated with β-glucosidase. To isolate and purify the isoflavone derivative from the resultant extract, C18 silica gel chromatograph was performed as above. Consequently, two isoflavone derivatives obtained by transforming the four isoflavone glycosides due to β-glucosidase were respectively isolated. Thus, total 6 isoflavone derivatives were respectively isolated.

<3-2> Isolation and Purification of Isoflavone Derivative from Soybean Stems

Isolation and purification of the isoflavone derivative in the ethanol extract of soybean stems having high isoflavone content obtained through the method described in Example <2-2> was performed by using MPLC (Teledyne Isco CombiFlash Companion). As a column material, C18 silica gel (YMC, 50 μm) was used. As an elution condition, water/acetonitrile mixed solution was used such that gradient elution in which acetonitrile solvent is increased from 0-90% was applied. As a result, four isoflavone derivatives were respectively isolated.

Further, the ethanol extract of soybean stems having high isoflavone derivative content obtained through the method described in Example <2-2> was treated with β-glucosidase. To isolate and purify the isoflavone derivative from the resultant extract, C18 silica gel chromatograph was performed. Consequently, two isoflavone derivatives obtained by transforming the four isoflavone glycosides due to β-glucosidase were respectively isolated. Thus, total 6 isoflavone derivatives were respectively isolated.

EXAMPLE 4

Structural Analysis of Isolated Isoflavone Derivative

To analyze 6 isoflavone derivative compounds isolated through the method described in <Example 3>, HPLC, UPLC/Q-TOF MS and NMR spectroscope analysis were performed.

Consequently, as shown in FIG. 4 and FIG. 12, peak 1 among 6 isoflavone derivatives was identified as daidzin represented by the following [Formula 2] (FIGS. 4 and 12).

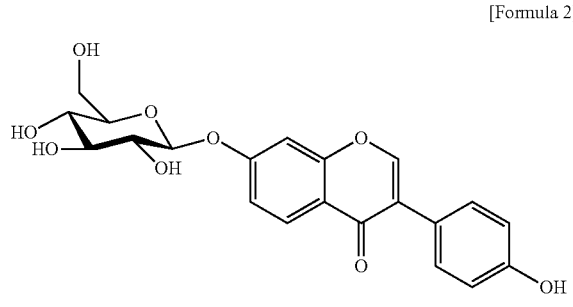

[Formula 2]

Daidzin (peak 1): ESI-MS(Q-TOF) [M+H]+ 417.1186 (calc. 417.1186, C21H21O9, 0.0 ppm); 1H NMR (500 MHz, DMSO-d6) δ 3.30 (2H, m, H-4", 2"), 3.47 (3H, m, H-3", H-5", 6"b), 3.73 (1H, dd, J=14.2, 7.4 Hz, H-6"a), 5.12 (1H, m, H-1"), 6.82 (2H, d, J=8.6 Hz, H-3', 5'), 7.15 (1H, dd, J=8.6, 2.1 Hz, H-6), 7.24 (1H, d, J=2.1 Hz, H-8), 7.41 (2H, d, J=8.6 Hz, H-2', 6'), 8.04 (1H, d, J=8.9 Hz, H-5), 8.39 (1H, s, H-2), and 9.56 (1H, s, 4'-OH); 13C NMR (125 MHz, DMSO-d6) δ 61.1 (C-6"), 70.1 (C-4"), 73.6 (C-2"), 76.9 (C-3"), 77.7 (C-5"), 100.5 (C-8), 104.5 (C-1"), 115.6 (C-3', 5'), 116.0 (C-6), 118.9 (C-4a), 122.8 (C-3), 124.2 (C-1'), 127.4 (C-5), 130.6 (C-2', 6'), 153.8 (C-2), 157.5 (C-4'), 157.7 (C-8a), 161.9 (C-7), 175.2 (C-4).

In addition, as shown in FIGS. 5 and 13, peak 2 was identified as genistin represented by the following [Formula 3] (FIGS. 5 and 13).

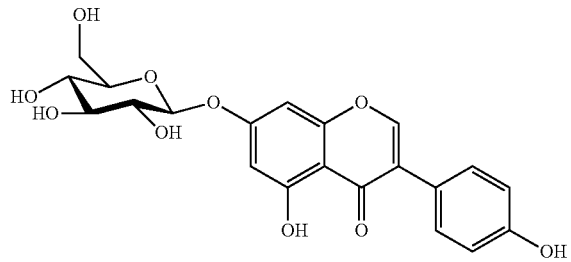

[Formula 3]

Genistin (peak 2): ESI-MS(Q-TOF) [M+H]+ 433.1139 (calc. 433.1135, C21H21O10, 0.9 ppm); 1H NMR (500 MHz, DMSO-d6) δ 3.19 (1H, dd J=9.9, 4.8 Hz, H-4"), 3.29 (1H, dd, m, J=13.4, 7.4 Hz, H-2"), 3.32 (1H, dd, J=13.4, 4.8 Hz, H-3"), 3.45 (1H, m, H-5"), 3.48 (1H, dd, J=11.4, 5.5 Hz, H-6"b), 3.73 (1H, dd, J=11.4, 4.8 Hz, H-6"a), 5.06 (1H, d, J=7.4 Hz, H-1"), 6.49 (1H, d, J=2.1 Hz, H-6), 6.72 (1H, d, J=2.1 Hz, H-8), 6.84 (2H, d, J=6.6 Hz, H-3', 5'), 7.41 (2H, d, J=6.6 Hz, H-2', 6'), 8.41 (1H, s, H-2), 9.53 (1H, s, 4'-OH), and 12.9 (1H, s, 5-OH). 13C NMR (125 MHz, DMSO-d6) δ 61.1 (C-6"), 70.1 (C-4"), 73.6 (C-2"), 76.9 (C-3"), 77.6 (C-5"), 95.0 (C-8), 100.0 (C-6), 100.4 (C-1"), 106.5 (C-4a), 115.5 (C-3', 5'), 121.4 (C-3), 123.0 (C-1'), 130.5 (C-2', 6'), 154.9 (C-2), 157.6 (C-4'), 157.9 (C-8a), 162.0 (C-5), 163.4 (C-7), 180.9 (C-4).

Further, as shown in FIGS. 6 and 14, peak 3 among 6 isoflavone derivatives was identified as malonyldaidzin represented by the following [Formula 4] (FIGS. 6 and 14).

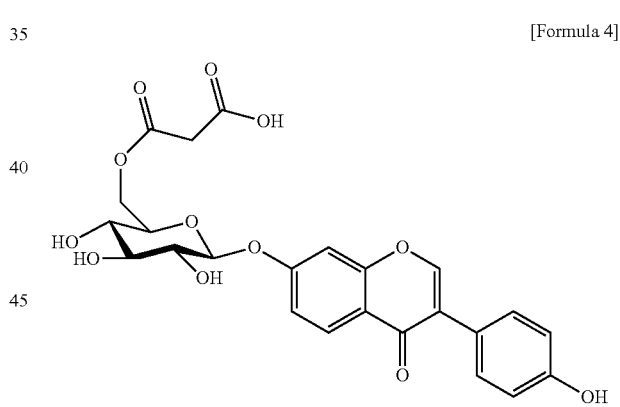

[Formula 4]

Malonyldaidzin (peak 3): ESI-MS(Q-TOF) [M+H]+ 503.1190 (calc. 503.1190, C24H23O12, 0.0 ppm); 1H NMR (500 MHz, DMSO-d6) δ 3.17 (2H, m, malonyl-CH2), 3.19 (1H, m, H-4"), 3.34 (1H, m, H-2"), 3.38 (1H, m, H-3"), 3.75 (H-5"), 4.14 (1H, m, H-6"b), 4.34 (1H, m, H-6"a), 5.14 (1H, d, J=7.6 Hz, H-1"), 6.52 (2H, d, J=8.2 Hz, H-3', 5'), 6.74 (1H, d, J=8.9 Hz, H-6), 7.04 (1H, s, H-8), 7.38 (2H, d, J=8.2 Hz, H-2', 6'), 7.95 (1H, d, J=8.9 Hz, H-5), 8.42 (1H, s, H-2). 13C NMR (125 MHz, DMSO-d6) δ 41.9 (malonyl-CH2), 64.2 (C-6"), 67.3 (C-4"), 71.4 (C-2"), 72.9 (C-5"), 75.6 (C-3"), 95.7 (C-8), 100.2 (C-1"), 102.2 (C-6), 106.5 (C-3', 5'), 113.1 (C-4a), 120.4 (C-3), 121.9 (C-1'), 130.2 (C-2', 6'), 157.6 (C-2), 154.8 (C-4'), 162.2 (C-8a), 161.9 (C-7), 166.8 (malonyl-COOR), 169.5 (malonyl-COOH), 179.9 (C-4).

Also, as shown in FIGS. 7 and 15, peak 4 among 6 isoflavone derivatives was identified as malonylgenistin represented by the following [Formula 5] (FIGS. 7 and 15).

[Formula 5]

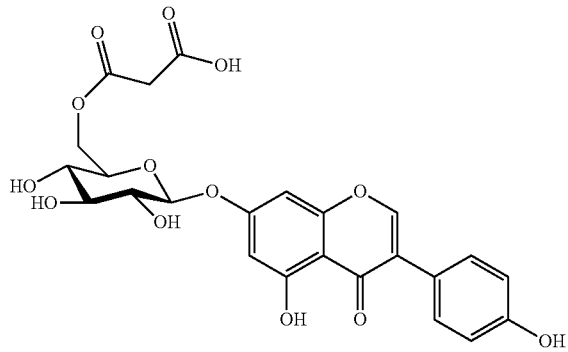

Malonylgenistin (peak 4): ESI-MS(Q-TOF) [M+H]+ 519.1138 (calc. 519.1139, C24H23O13, −0.2 ppm); 1H NMR (500 MHz, DMSO-d6) δ 3.19 (2H, m, malonyl-CH2), 3.20 (1H, m, H-4"), 3.28 (1H, m, H-2"), 3.33 (1H, m, H-3"), 4.12 (1H, m, H-6"b), 4.35 (1H, m, H-6"a), 5.12 (1H, d, J=7.7 Hz, H-1"), 6.46 (1H, s, H-6), 6.71 (1H, s, H-8), 6.83 (2H, d, J=8.1 Hz, H-3', 5'), 7.39 (2H, d, J=8.1 Hz, H-2', 6'), 8.40 (1H, s, H-2). 13C NMR (125 MHz, DMSO-d6) δ 41.6 (malonyl-CH2), 63.9 (C-6"), 69.4 (C-4"), 72.7 (C-2"), 73.6 (C-5"), 76.1 (C-3"), 94.3 (C-8), 99.3 (C-1"), 99.4 (C-6), 106.0 (C-4a), 115.0 (C-3', 5'), 120.9 (C-1'), 122.5 (C-3), 130.2 (C-2', 6'), 154.6 (C-2), 157.1 (C-8a), 157.4 (C-4'), 162.2 (C-5), 162.6 (C-7), 167.0 (malonyl-COOR), 167.5 (malonyl-COOH), 180.5 (C-4).

Further, as shown in FIGS. 8 and 16, one of 6 isoflavone derivatives transformed from the 4 isoflavone derivatives was identified as daidzein represented by the following [Formula 6] (FIGS. 8 and 16).

[Formula 6]

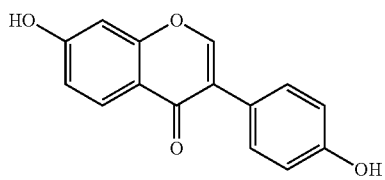

Daidzein: ESI-MS(Q-TOF) [M+H]+ 255.0658 (calc. 255.0657, C15H11O4, 0.4 ppm); 1H NMR (500 MHz, DMSO-d6) δ 6.84 (2H, d J=8.6 Hz, H-3', 5'), 6.85 (1H, d, J=2.0 Hz, H-8), 6.96 (1H, dd, J=8.8, 2.2 Hz, H-6), 7.38 (2H, d, J=8.6 Hz, H-2', 6'), 8.07 (1H, d, J=8.8 Hz, H-5), 8.15 (1H, s, H-2). 13C NMR (125 MHz, DMSO-d6) δ 102.5 (C-8), 115.4 (C-6), 115.6 (C-3', 5'), 117.0 (C-4a), 123.0 (C-1'), 123.9 (C-3), 127.7 (C-5), 130.5 (C-2', 6'), 153.2 (C-2), 157.6 (C-4'), 157.9 (C-8a), 163.1 (C-7), 175.1 (C-4).

Also, as shown in FIGS. 8 and 16, one of 6 isoflavone derivatives transformed from the 4 isoflavone derivatives was identified as genistein represented by the following [Formula 7] (FIGS. 8 and 16).

[Formula 7]

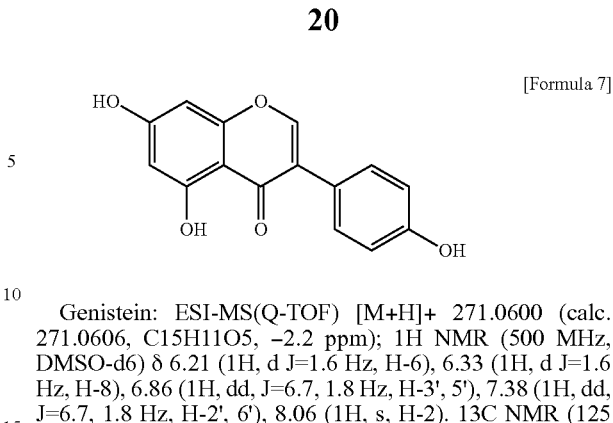

Genistein: ESI-MS(Q-TOF) [M+H]+ 271.0600 (calc. 271.0606, C15H11O5, −2.2 ppm); 1H NMR (500 MHz, DMSO-d6) δ 6.21 (1H, d J=1.6 Hz, H-6), 6.33 (1H, d J=1.6 Hz, H-8), 6.86 (1H, dd, J=6.7, 1.8 Hz, H-3', 5'), 7.38 (1H, dd, J=6.7, 1.8 Hz, H-2', 6'), 8.06 (1H, s, H-2). 13C NMR (125 MHz, DMSO-d6) δ 94.0 (C-8), 99.3 (C-6), 104.8 (C-4a), 115.4 (C-3', 5'), 121.6 (C-3), 122.7 (C-1'), 130.5 (C-2', 6'), 154.3 (C-2), 157.8 (C-4'), 158.0 (C-8a), 162.4 (C-5), 164.7 (C-7), 180.6 (C-4)

EXAMPLE 5

Quantitative Analysis of Isoflavone Derivative Using UPLC

<5-1> Quantitative Analysis of 4 Isoflavone Derivatives Isolated from Soybean Leaves To quantitative analyze 4 isoflavone compounds isolated through the method described in Example <3-1> and 4 isoflavone compounds isolated from soybean leaves treated with ethephon after harvest, UPLC was used.

Specifically, for UPLC, ACQUITY UPLC™ system (from Waters Co., USA) was used. As a column, ODS-based BEH C18 (100×2.1 mm) was used. As a mobile phase, water containing 0.1% acetic acid and acetonitrile containing 0.1% acetic acid were used. Gradient elution in which the acetonitrile solvent was increased from 3% at initial to 57% for 15 minutes was applied. A flow rate was adjusted to 0.4 ml/min. An injected amount of the extraction solution was 2 ul. A detection wavelength for analysis was 254 nm. 4 isoflavone compounds isolated through the method described in <Example 3> were dissolved in methanol to prepare standard solutions in a range from 1-100 ug/ml. Then, UPLC analysis was performed and a calibration curve was prepared from the peak area. The stand materials of isoflavone used in the analysis were four, i.e., didzin, genistin, malonyldaidzin, malonylgenistin all of which had high purity of at least 98% (Table 1).

Further, soybean leaves of soybean plants after 10-90 days of seeding of Example <1-1> were taken and treated with 50 ppm of ethephon. Then, the 4 isoflavone derivatives were isolated through the method described in Example <3-1>, and thereafter quantitative analysis was performed as above (Table 2).

Consequently, as shown in FIG. 1, it has been found that, in the ethanol fraction of soybean leaves without ethephon treatment, the isoflavone derivative was not detected, while, in the ethanol fraction of soybean leaves treated with 50 ppm of ethephon, 4 isoflavone derivative contents were rapidly increased. In particular, after 7 days of the ethephon treatment, isoflavone content was reached the highest level of 17073 ug/g (Table 1).

Further, as shown in Table 2, it has been found that soybean leaves treated with ethephon after harvest showed rapidly increased isoflavone derivative content as soybean leaves harvested after ethephon treatment (Table 2). Thus, from the result, it has been found that soybean leaves having high isoflavone derivative content may be prepared through the method of treating soybean leaves with ethephon after harvest, as well as the method of harvesting soybean leaves after ethephon treatment.

TABLE 1

| Isoflavone | Content (ug/g) | | | | |
|---|---|---|---|---|---|
| | Untreated | 1 day after treatment | 3 days after treatment | 5 days after treatment | 7 days after treatment |
| Daidzin (1) | undected | 1428.3 ± 42.4 | 1938.2 ± 71.3 | 2538.0 ± 74.9 | 2759.5 ± 82.4 |
| Genistin (2) | undected | 1463.4 ± 38.2 | 2254.3 ± 76.1 | 2648.3 ± 68.2 | 2863.7 ± 94.1 |
| Malonyldaidzin (3) | undected | 2569.6 ± 50.8 | 3615.2 ± 93.5 | 4423.7 ± 149.5 | 5688.6 ± 171.2 |
| Malonylgenistin (4) | undected | 2608.7 ± 57.1 | 4275.9 ± 120.7 | 4899.4 ± 141.2 | 5761.5 ± 136.5 |
| Total isoflavone | — | 8070.0 ± 189 | 12083.6 ± 362 | 14512.4 ± 434 | 17073.3 ± 484 |

TABLE 2

| Isoflavone | Content (ug/g) | | | |
|---|---|---|---|---|
| | Untreated | 1 day after treatment | 2 days after treatment | 3 days after treatment |
| Daidzin (1) | undected | 1280.4 ± 22.9 | 1551.2 ± 31.4 | 1991.5 ± 51.8 |
| Genistin (2) | undected | 1316.7 ± 27.5 | 1803.4 ± 48.2 | 2098.7 ± 56.2 |
| Malonyldaidzin (3) | undected | 2312.1 ± 33.4 | 3337.9 ± 56.2 | 3528.4 ± 94.1 |
| Malonylgenistin (4) | undected | 2347.4 ± 37.2 | 3480.6 ± 72.4 | 3909.2 ± 91.7 |
| Total isoflavone | — | 7256.6 ± 121 | 10173.1 ± 208 | 11527.8 ± 294 |

<5-2> Quantitative Analysis of 4 Isoflavone Compounds Isolated from Soybean Stems To quantitative analyze 4 isoflavone compounds isolated through the method described in Example <3-2>, HPLC was used.

Specifically, for HPLC, HPLC Series 200 system (from Perkinelmer Co., USA) was used. As a column, ODS-based Zolbox Bonus-RP (150×4.6 mm) was used. As a mobile phase, water containing 0.1% acetic acid and acetonitrile containing 0.1% acetic acid were used. Gradient elution in which the acetonitrile solvent was increased from 5% at initial to 95% for 85 minutes was applied. A flow rate was adjusted to 1 ml/min. An injected amount of the extraction solution was 10 ul. A detection wavelength for analysis was 254 nm. 4 isoflavone compounds isolated through the method described in Example <3-2> were dissolved in methanol to prepare standard solutions in a range from 1-100 ul/ml. Then, HPLC analysis was performed and a calibration curve was prepared from the peak area. The stand materials of isoflavone used in the analysis were four, i.e., didzin, genistin, malonyldaidzin, malonylgenistin all of which had high purity of at least 98% (Table 3).

Consequently, as shown in Table 3, it has been found that, in the ethanol fraction of soybean stems without ethylene treatment, the isoflavone derivative was not detected, while, in the ethanol fraction of soybean stems treated with 100-1000 ppm of ethylene, 4 isoflavone derivative contents were rapidly increased. In particular, after the ethylene treatment, total isoflavone content was reached the highest level of 11951 ug/g (Table 3).

TABLE 3

| Isoflavone | Content (ug/g) | |
|---|---|---|
| | Untreated | After treatment |
| Daidzin (1) | Undetected | 1931.7 ± 71.2 |
| Genistin (2) | Undetected | 2004.6 ± 86.1 |
| Malonyldaidzin (3) | Undetected | 3982.0 ± 129.2 |
| Malonylgenistin (4) | Undetected | 4033.1 ± 156.5 |
| Total isoflavone | — | 11951.3 ± 443 |

Hereinafter, Preparation Examples for the composition of the present invention are described.

PREPARATION EXAMPLE 1

Preparation of Pharmaceutical Composition

<1-1> Preparation of Powder

| | |
|---|---|
| Soybean leaves and soybean stems having high isoflavone derivative content of the present invention, an extraction thereof or fraction of the extract | 0.1 g |
| Lactose | 1.5 g |
| Talc | 0.5 g |

The ingredients above were mixed and filled to a sealed bag to prepare powder.

<1-2> Preparation of Tablet

| | |
|---|---|
| Soybean leaves and soybean stems having high isoflavone derivative content of the present invention, an extraction thereof or fraction of the extract | 0.1 g |
| Lactose | 7.9 g |
| Crystalline cellulose | 1.5 g |
| Magnesium stearate | 0.5 g |

After mixing the ingredients above, a tablet was prepared through a direct tableting method.

<1-3> Preparation of Capsule

| | |
|---|---|
| Soybean leaves and soybean stems having high isoflavone derivative content of the present invention, an extraction thereof or fraction of the extract | 0.1 g |
| Corn starch | 5 g |
| Carboxy cellulose | 4.9 g |

After preparing powder by mixing the ingredients above, a capsule was prepared by filling a hard capsule with the powder according to the typical method for preparing a capsule.

<1-4> Preparation of Injection Formulation

| | |
|---|---|
| Soybean leaves and soybean stems having high isoflavone derivative content of the present invention, an extraction thereof or fraction of the extract | 0.1 g |
| Injectable sterilized water | appropriate amount |
| pH adjuster | appropriate amount |

According to the typical method for preparing an injection formulation, preparation was performed to have 2 ml of the ingredients above per one ampoule.

<1-5> Preparation of Liquid Formulation

| | |
|---|---|
| Soybean leaves and soybean stems having high isoflavone derivative content of the present invention, an extraction thereof or fraction of the extract | 0.1 g |
| Isomerized sugar | 10 g |
| Mannitol | 5 g |
| Purified water | appropriate amount |

According to the typical method for preparing a liquid formulation, each ingredient was added and dissolved in purified water. Then, an appropriate amount of lemon flavor was added and the ingredients above were mixed. Thereafter, purified water was added to adjust a total volume to 100 ml, and then the resultant was filled to a brown bottle and sterilized to prepare a liquid formulation.

PREPARATION EXAMPLE 2

Preparation of Health Food

<2-1> Preparation of Mixed Tea

Soybean leaves and soybean stems having high isoflavone derivative content of the present invention, an extraction thereof or fraction of the extract were mixed with a herb plant having flavor to prepare mixed tea.

<2-2> Preparation of Wheat Food 0.5-5.0 parts by weight of soybean leaves and soybean stems having high isoflavone derivative content of the present invention, an extraction thereof or fraction of the extract was added to wheat, and mixed. By using the mixture, bread, cake, cookies, crackers, and noodles were prepared.

<2-3> Preparation of Soup and Gravies 0.1-5.0 parts by weight of the soybean leaves and soybean stems having high isoflavone derivative content of the present invention, an extraction thereof or fraction of the extract was added to soup and gravies to prepare soup and gravies of livestock processed products, and noodles for enhancing health.

<2-4> Preparation of Ground Beef 10 parts by weight of the soybean leaves and soybean stems having high isoflavone derivative content of the present invention, an extraction thereof or fraction of the extract was added to ground beef to prepare ground beef for enhancing health.

<2-5> Preparation of Dairy Products 5-10 parts by weight of the soybean leaves and soybean stems having high isoflavone derivative content of the present invention, an extraction thereof or fraction of the extract was added to milk, and various dairy products such as butter and ice cream were prepared by using the milk.

<2-6> Preparation of Sunsik (Grain Powder)

Brown rice, barley, glutinous rice, and adlay were subjected to pre gelatinization through the known method, and dried. Then, the resultant was roasted and pulverized to powder having a particle size of 60 mesh with a pulverizer.

Black beans, black sesame, and *perilla* seeds were also steamed through the known method, and dried. Then, the resultant was roasted and pulverized to powder having a particle size of 60 mesh with a pulverizer.

The soybean leaves and soybean stems having high isoflavone derivative content of the present invention, the extraction thereof or fraction of the extract were concentrated under reduced pressure in a vacuum concentrator. Then, the resultant was dried with a spray, hot air drier, and the resultant dried product was pulverized to have a particle size of 60 mesh to obtain dried powder.

The grains, seeds, and soybean leaves and soybean stems having high isoflavone derivative content of the present invention, the extraction thereof or fraction of the extract prepared above were mixed in the following ratio for preparation.

Grains (brown rice 30 parts by weight, adlay 15 parts by weight, barley 20 parts by weight), Seeds (*perilla* seeds 7 parts by weight, black beans 8 parts by weight, black sesame 7 parts by weight), Soybean leaves and soybean stems having high isoflavone derivative content of the present invention, the extraction thereof or fraction of the extract (3 parts by weight),

*Ganoderma lucidum* (0.5 parts by weight), Rhemannia (0.5 parts by weight)

PREPARATION EXAMPLE 3

Preparation of Health Beverage

| | |
|---|---|
| Soybean leaves and soybean stems having high isoflavone derivative content of the present invention, an extraction thereof or fraction of the extract | 100 mg |
| citric acid | 100 mg |
| Oligosaccharide | 100 mg |
| Plum Concentrate | 2 mg |
| Taurine | 100 mg |

Purified water was added to adjust a total volume of 500 ml.

The ingredients above were mixed according to the typical method for preparing a health beverage. Then, the mixture was heat-stirred at 85° C. for about 1 hour. Thereafter, the resultant solution was filtered and filled to a sterilized 1 l vessel. The vessel was sealed and sterilized and cold stored to be used to prepare the health beverage composition of the present invention.

The composition ratio is a preferable example in which ingredients relatively suitable to favorite beverage were mixed and compounded. However, the composition ratio may be varied depending on regional and ethnic favorite including user class, user country, and purpose of use.

PREPARATION EXAMPLE 4

Preparation of Cosmetic Composition

<4-1> Preparation of Cream

| | |
|---|---|
| Soybean leaves and soybean stems having high isoflavone derivative content of the present invention, an extraction thereof or fraction of the extract | 4.6 parts by weight |
| Cetostearyl alcohol | 2.8 parts by weight |
| Wax | 2.6 parts by weight |
| Stearic acid | 1.4 parts by weight |
| Lipophilicmonostearic acid glycerin | 2 parts by weight |
| PEG-100 stearate | 1 parts by weight |
| Sesquioleate sorbitan | 1.4 parts by weight |
| Jojoba oil | 4 parts by weight |
| Squalane | 3.8 parts by weight |
| Polysorbate 60 | 1.1 parts by weight |
| Macadamia nut oils | 2 parts by weight |
| Tocopherol acetate | 0.2 parts by weight |
| Methyl polysiloxane | 0.4 parts by weight |
| Ethyl paraben | 0.1 parts by weight |
| Propyl paraben | 0.1 parts by weight |
| Euxyl K-400 | 0.1 parts by weight |
| 1,3-Butylene glycol | 7 parts by weight |
| Methyl paraben | 0.05 parts by weight |
| Glycerin | 6 parts by weight |
| d-panthenol | 0.2 parts by weight |
| Triethanolamine | 0.2 parts by weight |
| pt 41891 | 0.2 parts by weight |
| p-H2O | 46.05 parts by weight |

<4-2> Preparation of Lotion

| | |
|---|---|
| Soybean leaves and soybean stems having high isoflavone derivative content of the present invention, an extraction thereof or fraction of the extract | 3.5 parts by weight |
| Cetostearyl alcohol | 1.6 parts by weight |
| Stearic acid | 1.4 parts by weight |
| Lipophilicmonostearic acid glycerin | 1.8 parts by weight |
| PEG-100 stearate | 2.6 parts by weight |
| Sesquioleate sorbitan | 0.6 parts by weight |
| Squalene | 4.8 parts by weight |
| Macadamia nut oils | 2 parts by weight |
| Jojoba oil | 2 parts by weight |
| Tocopherol acetate | 0.4 parts by weight |
| Methyl polysiloxane | 0.2 parts by weight |
| Ethyl paraben | 0.1 parts by weight |
| Propyl paraben | 0.1 parts by weight |
| 1,3-Butylene glycol | 4 parts by weight |
| Methyl paraben | 0.1 parts by weight |
| Xanthan gum | 0.1 parts by weight |
| Glycerin | 4 parts by weight |
| d-panthenol | 0.15 parts by weight |
| Allantoin | 0.1 parts by weight |
| Carbona(2% aq. Sol) | 4 parts by weight |
| Triethanolamine | 0.15 parts by weight |
| Ethanol | 3 parts by weight |
| pt 41891 | 0.1 parts by weight |
| p-H20 | 48.3 parts by weight |

We claim:

1. A method for preparing a soybean leaf or soybean stem having increased content of isoflavone derivatives represented by [Formula 2] to [Formula 5], compared to untreated soybean leaf or soybean stem, comprising treating the soybean leaf or soybean stem with ethylene, an ethylene donor, or an ethylene generator in a concentration of 5 to 1000 ppm:

[Formula 2]

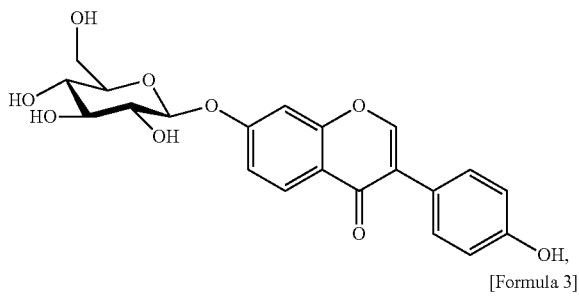

[Formula 3]

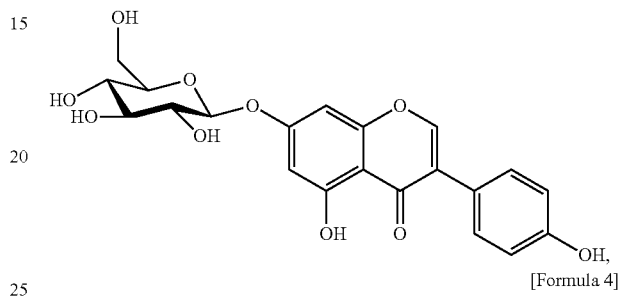

[Formula 4]

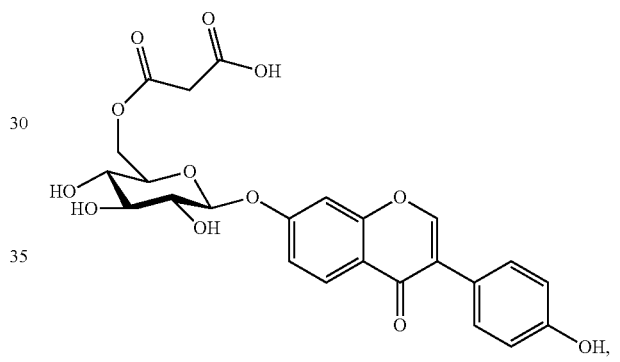

and

[Formula 5]

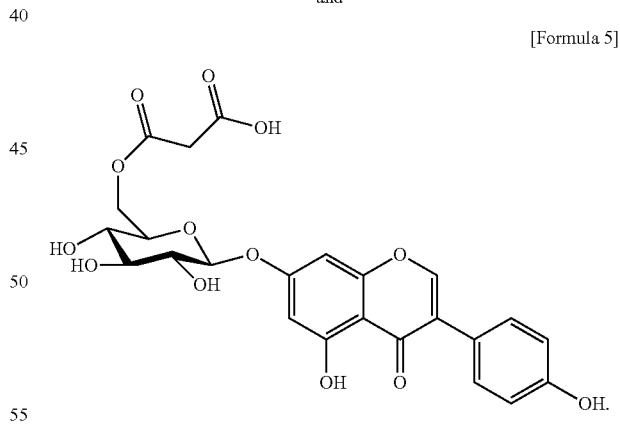

2. The method for preparing a soybean leaf or soybean stem according to claim 1, wherein the soybean leaf or soybean stem is 10 to 90 days after seeding.

3. The method for preparing a soybean leaf or soybean stem according to claim 1, wherein the ethylene donor is ethephon.

4. A method for preparing a soybean leaf or soybean stem extract comprising:

preparing an extract of soybean leaf or soybean stem by extracting the soybean leaf or soybean stem which is treated with ethylene, an ethylene donor, or an ethylene generator in a concentration of 5 to 1000 ppm; and treating the extract of soybean leaf or soybean stem with β-glucosidase.

5. The method for preparing a soybean leaf or soybean stem extract according to claim 4, wherein the β-glucosidase treated soybean leaf or soybean stem extract comprises isoflavone derivatives represented by [Formula 6] or [Formula 7]:

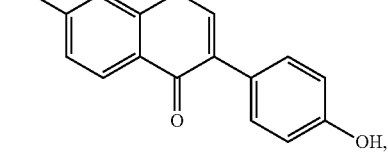
[Formula 6]

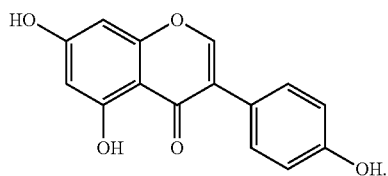
[Formula 7]

6. The method for preparing a soybean leaf or soybean stem according to claim 1, wherein the isoflavone derivatives are produced by:
   1) treating soybean leaves or soybean stems with ethylene, an ethylene donor, or an ethylene generator in a concentration of 5 to 500 ppm to prepare soybean leaves or soybean stems; and
   2) extracting the soybean leaves or soybean stems in step 1) and then isolating the isoflavone derivative represented by the [Formula 2] to [Formula 5].

7. A soybean leaf or soybean stem having increased content of isoflavone derivatives represented by the [Formula 2] to [Formula 5], compared to untreated soybean leaf or soybean stem, prepared by the method of claim 1.

8. A health food or cosmetic composition comprising the soybean leaf or soybean stem of claim 7 having increased content of isoflavone derivatives represented by the [Formula 2] to [Formula 5], compared to untreated soybean leaf or soybean stem, an extract of the soybean leaf or soybean stem, or a fraction of the extract.

9. A method of using the health food according to claim 8, wherein the health food is administered to a subject for treating osteoporosis, heart diseases, breast cancer, vaginal diseases, hyperlipidemia, skin aging and/or facial blushing.

10. A cosmetic composition comprising the soybean leaf or soybean stem of claim 7 having increased content of isoflavone derivatives represented by the [Formula 2] to [Formula 5], compared to untreated soybean leaf or soybean stem, an extract of the soybean leaf or soybean stem, or a fraction of the extract.

11. A method of using the cosmetic composition of claim 10, comprising applying the composition to the skin of a subject.

12. The soybean leaf or soybean stem made by the method of claim 1.

13. The composition of claim 8, wherein the composition is a health food composition.

14. The composition of claim 8, wherein the composition is a cosmetic composition.

* * * * *